US006310032B1

(12) United States Patent
Sprecker et al.

(10) Patent No.: US 6,310,032 B1
(45) Date of Patent: Oct. 30, 2001

(54) α-OXYGEN-SUBSTITUTED CYCLOHEXANE PROPIONITRILES, PERFUMERY USES THEREOF AND PROCESSES FOR PREPARING SAME

(75) Inventors: Mark A. Sprecker, Sea Bright; Richard A. Weiss, Livingston; Marie R. Hanna, Hazlet; Charles E. J. Beck, Summit, all of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/517,603

(22) Filed: Mar. 2, 2000

(51) Int. Cl.[7] .......... A61K 7/46

(52) U.S. Cl. .......... 512/6; 512/25; 558/430; 558/357; 558/371

(58) Field of Search .......... 512/6, 25; 558/430, 558/357, 371

(56) References Cited

U.S. PATENT DOCUMENTS

| | | | |
|---|---|---|---|
| 3,816,503 | 6/1974 | van Poelvoorde | 260/464 |
| 4,219,449 * | 8/1980 | Lenselink | 512/6 |
| 5,011,970 * | 4/1991 | Lenselink | 558/430 |
| 5,292,902 * | 3/1994 | Helmlinger | 549/458 |
| 5,917,067 | 6/1999 | Cotarca et al. | 554/132 |

FOREIGN PATENT DOCUMENTS

| | | | |
|---|---|---|---|
| 60152440 | 8/1985 | (JP) | C07C/59/185 |

OTHER PUBLICATIONS

Stork and Zhao, *Tetrahedron Letters*, vol. 30, No. 3, pp. 287–290 (1989) entitled "A Simple Method of Dethioacetalization".

Giese, et al, *Chem. Ber.*, 117, pp. 2132–2139 (1984) (publication receipt date Aug. 17, 1983) entitled "Diastereoselektivität der CC–Verknüpfung cyclischer Radikale".

Dufěÿ, *Bulletin De La Sociét´´Chimique De France*, 1968, No. 11, pp. 4653–4662 (manuscript received Nov. 22, 1967) entitled "Sur la prĕparation des alcoylhexahydrochromannols–2".

Tureček, *Collection Czechoslovak Chem. Commun.* [vol. 47], 1982, pp. 858–876 and entitled "Preparation of 7–Oxabicyclo[4.3.0]Nonanes and 2–Oxabicyclo[4.4.0]Decanes Specifically Labelled with Deuterium".

* cited by examiner

*Primary Examiner*—Jill Warden
*Assistant Examiner*—Monique T. Cole
(74) *Attorney, Agent, or Firm*—Joseph F. Leightner

(57) ABSTRACT

Described are α-oxygen-substituted cyclohexane propionitriles having the structure:

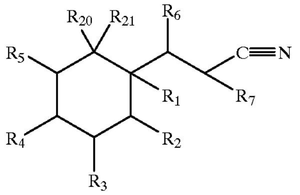

wherein $R_{20}$ and $R_{21}$ are the same or different $C_1$–$C_3$ lower alkoxy; or wherein $R_{20}$ is hydrogen and $R_{21}$ is hydroxy, $C_1$–$C_3$ lower alkoxy or $C_1$–$C_3$ lower acyloxy; and wherein $R_1$, $R_2$, $R_3$, $R_4$, $R_5$, $R_6$ and $R_7$ are the same or different hydrogen or $C_1$–$C_4$ lower alkyl, and uses thereof for their organoleptic properties in augmenting or enhancing or imparting aromas in or to perfume compositions, colognes, microporous polymers or perfumed articles including solid or liquid anionic, cationic, nonionic or zwitterionic detergents, fabric softener compositions, fabric softener articles, hair care compositions and the like.

19 Claims, 12 Drawing Sheets

FIG. 4 - A
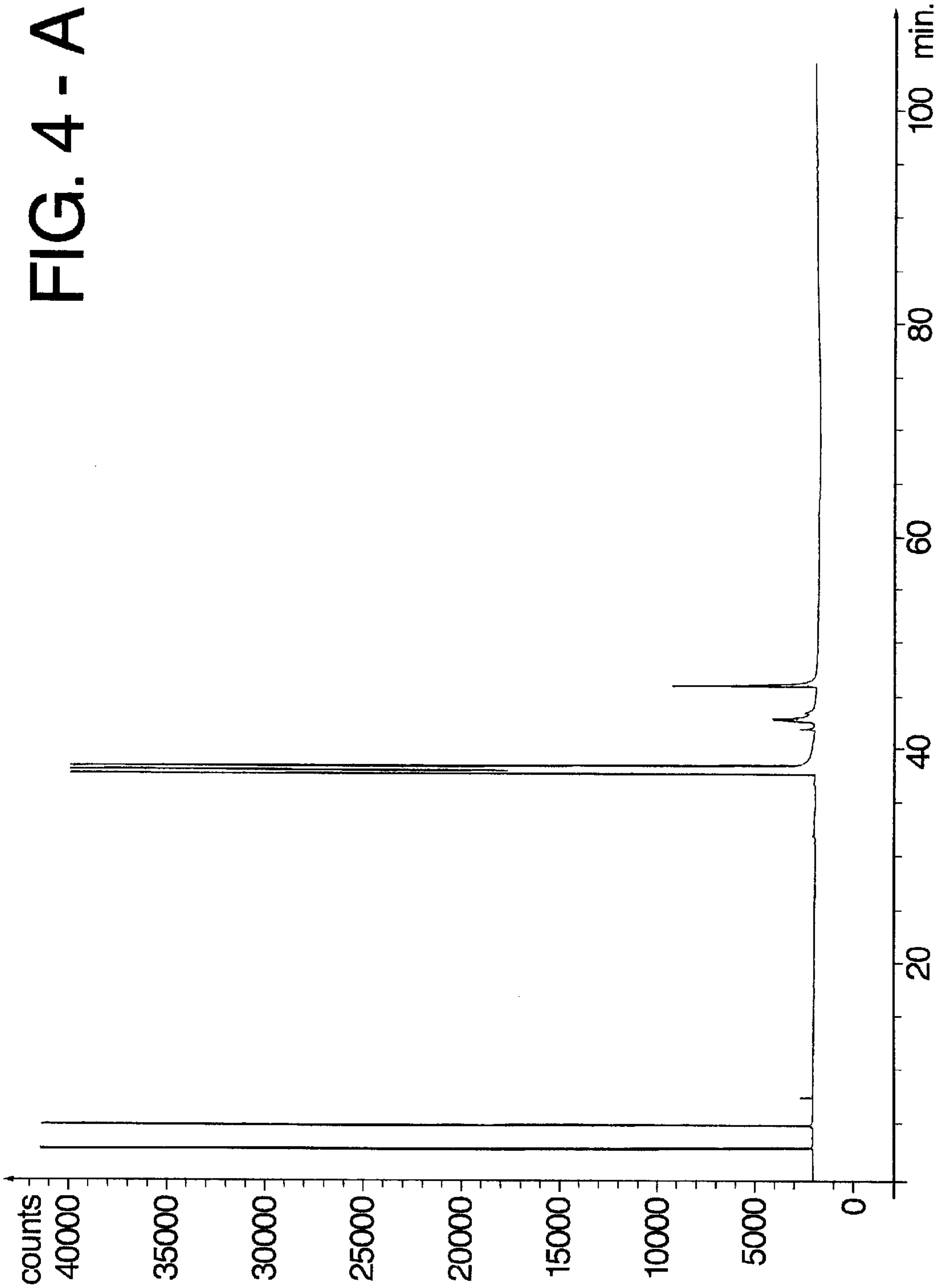

FIG. 4 - B
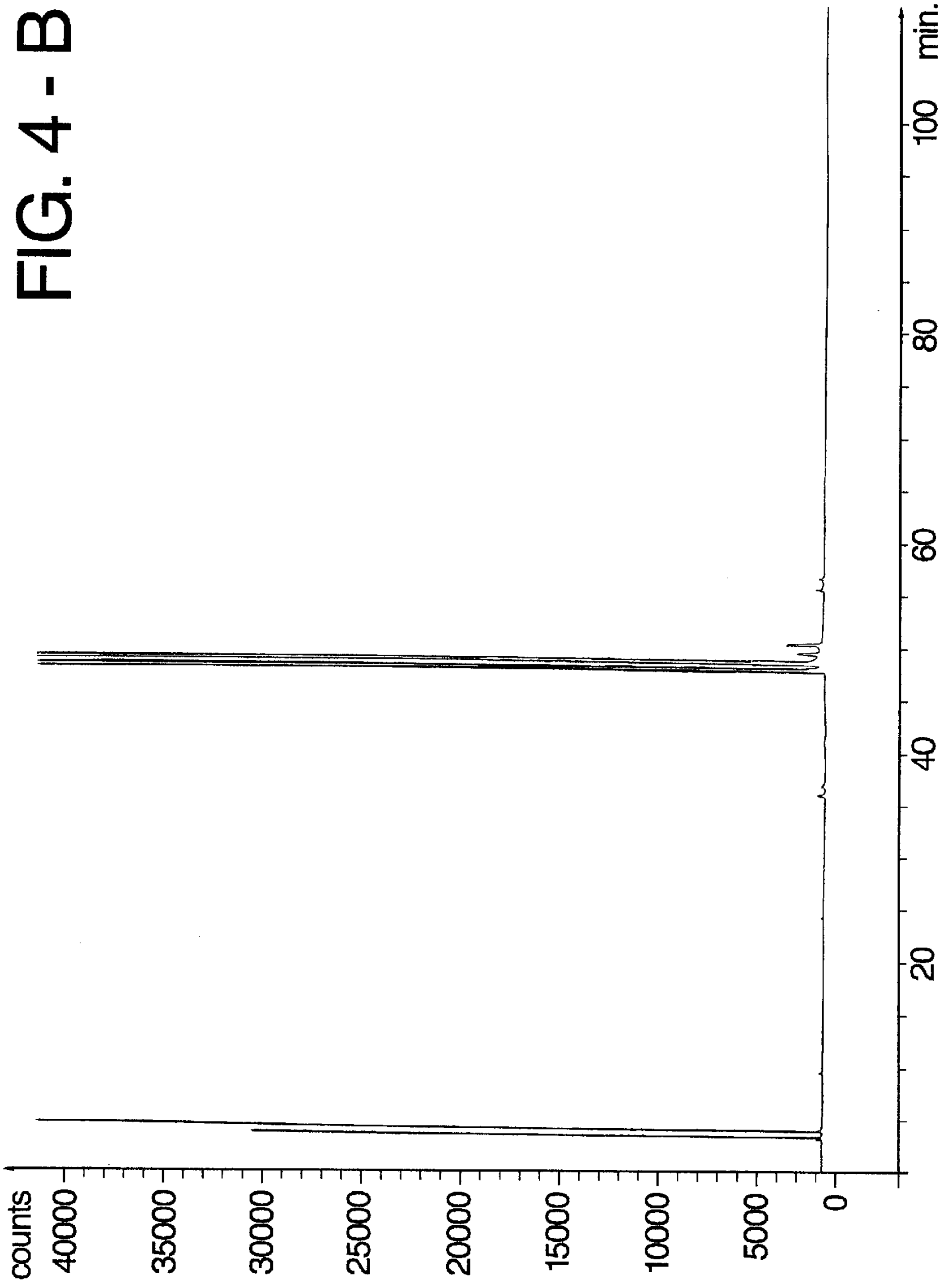

FIG. 7 - A
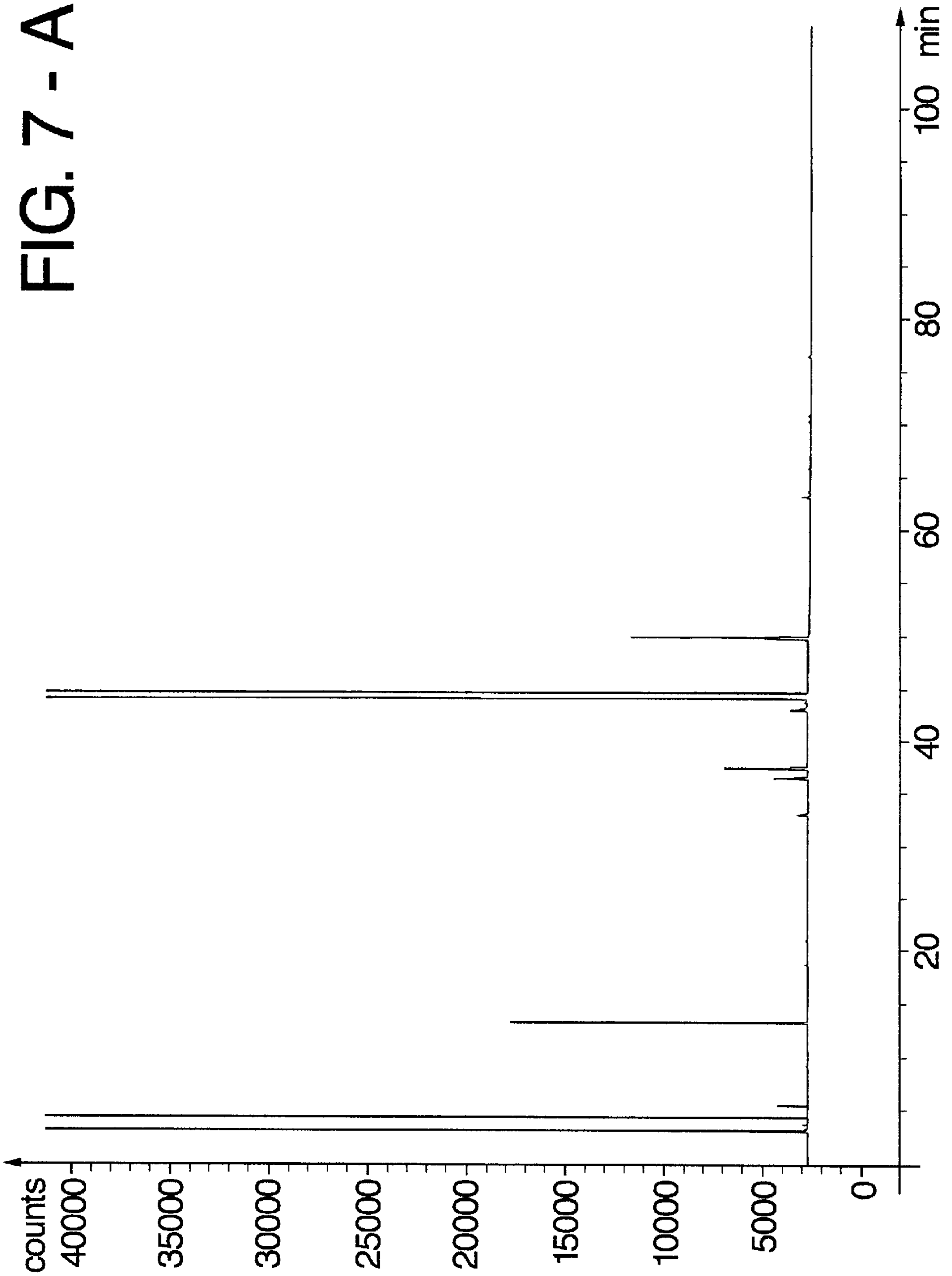

FIG. 7 - B
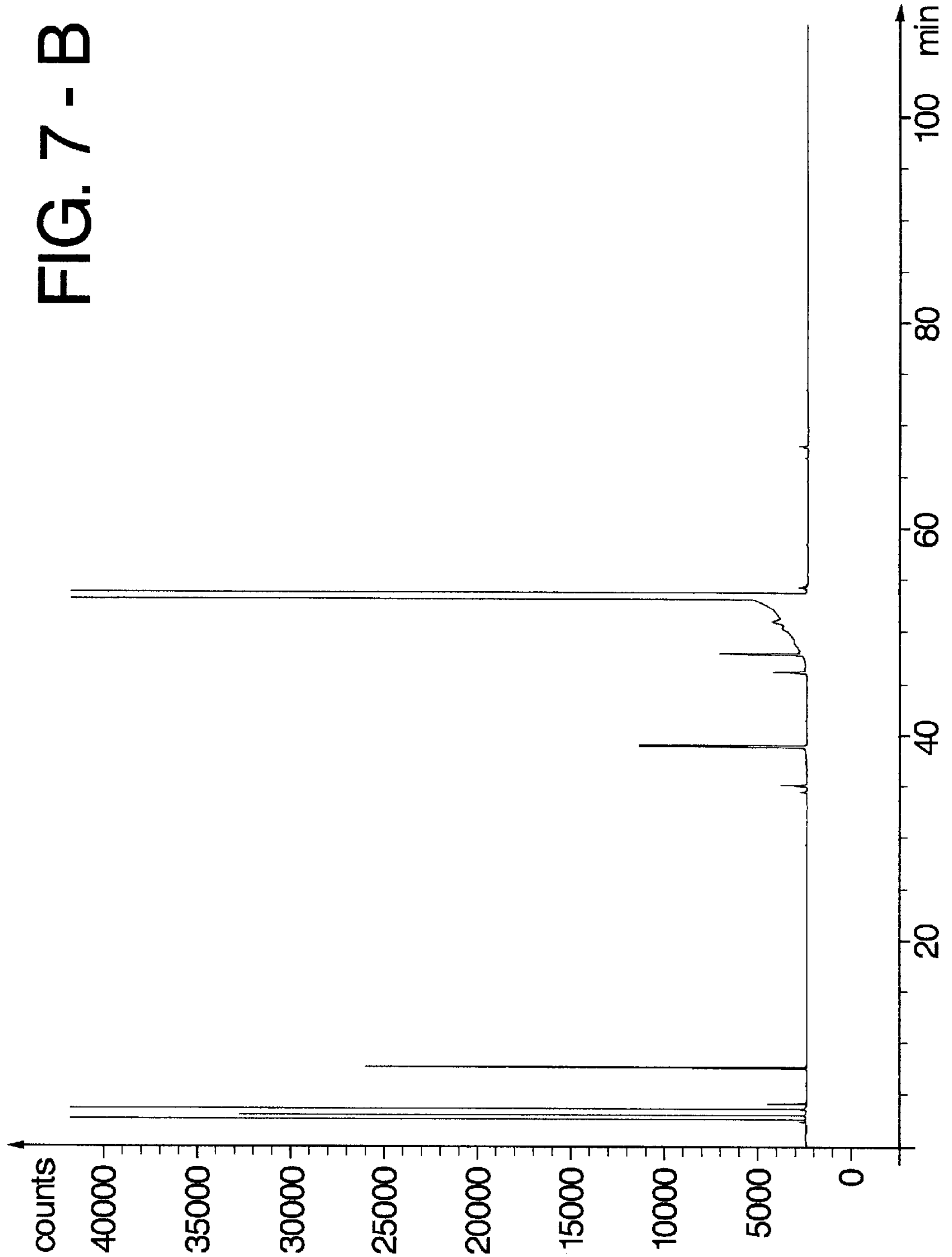

FIG. 10
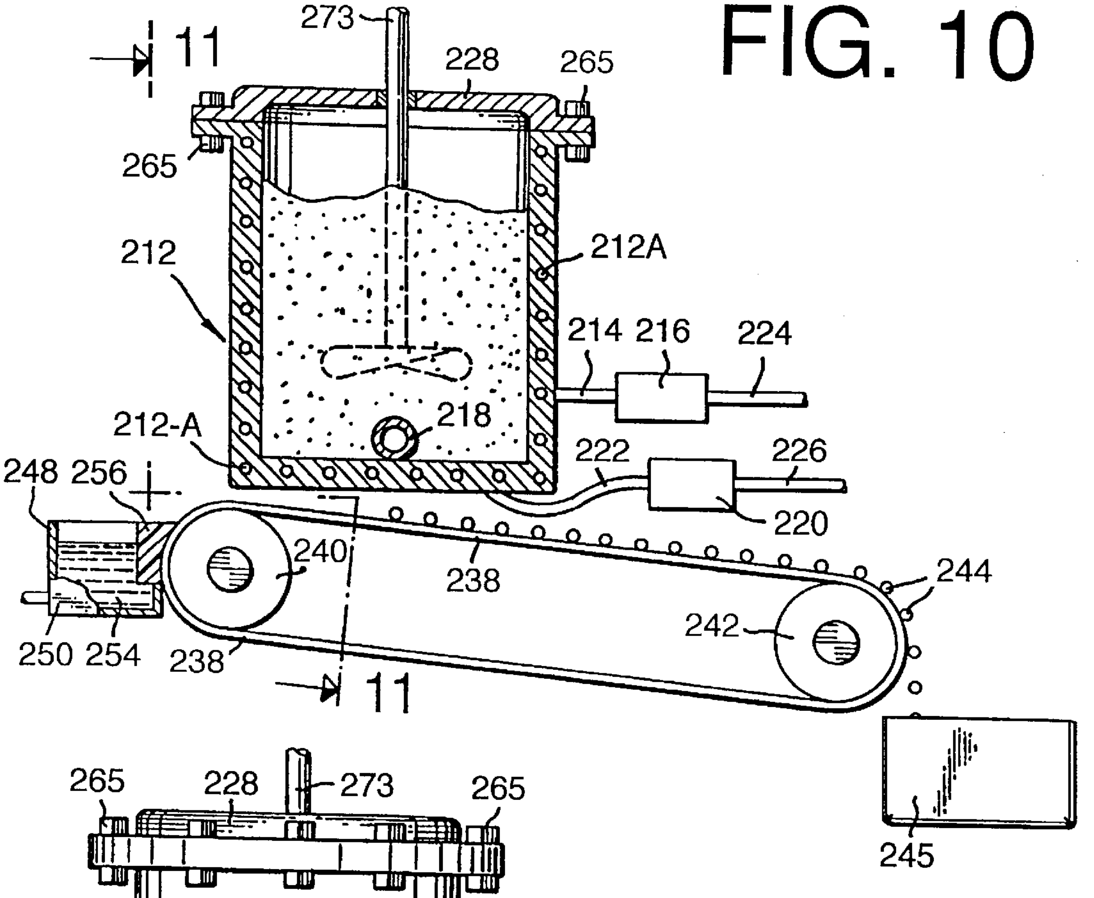
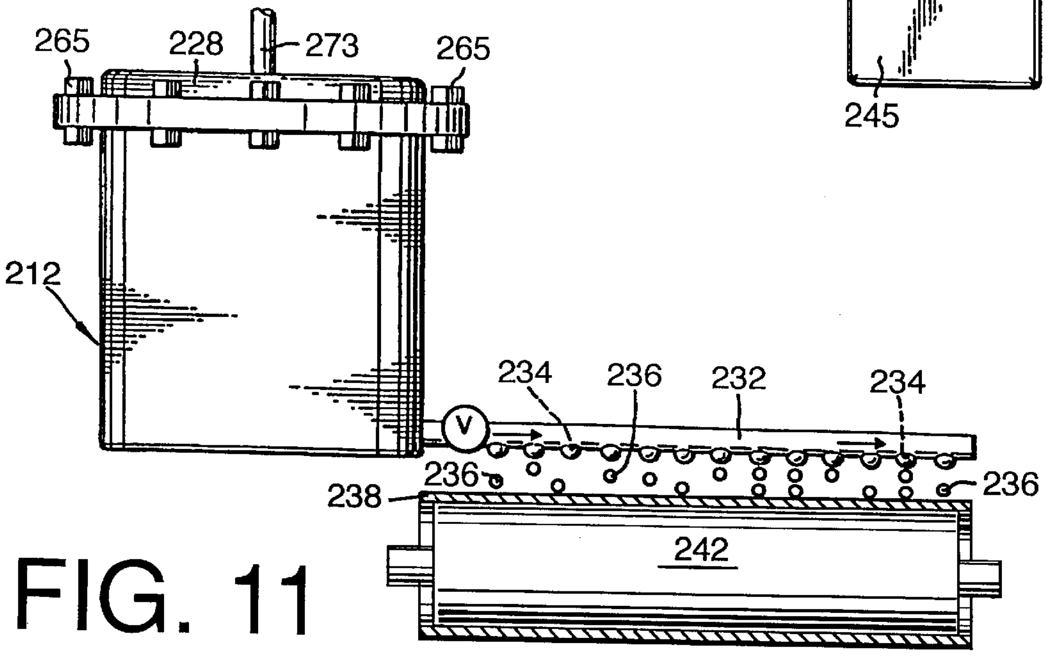
FIG. 11

α-OXYGEN-SUBSTITUTED CYCLOHEXANE PROPIONITRILES, PERFUMERY USES THEREOF AND PROCESSES FOR PREPARING SAME

BACKGROUND OF THE INVENTION

Our invention relates to α-oxygen-substituted cyclohexane propionitriles defined according to the structure:

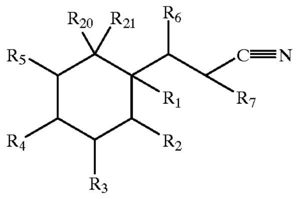

wherein $R_{20}$ and $R_{21}$ are the same or different $C_1$–$C_4$ lower alkoxy; or wherein $R_{20}$ is hydrogen and $R_{21}$ is hydroxy, $C_1$–$C_3$ lower alkoxy or $C_1$–$C_3$ lower acyloxy, processes for preparing same and perfumery uses thereof; and wherein $R_1$, $R_2$, $R_3$, $R_4$, $R_5$, $R_6$ and $R_7$ are the same or different hydrogen or $C_1$–$C_4$ lower alkyl.

Woody, orris, sweet, coumarinic aromas with spicy and soft floral undertones are particularly desirable in augmenting or enhancing the aroma of perfume compositions, colognes and perfumed articles (e.g., solid or liquid anionic, cationic, nonionic or zwitterionic detergents, fabric softener compositions, fabric softener articles, hair preparations, cosmetic powders and perfumed polymers).

Nitriles such as citronellyl nitrile have been known for use in augmenting or enhancing the aroma of perfume compositions, perfumed articles and colognes for a number of years.

Nothing in the prior art, however, discloses the α-oxygen-substituted cyclohexane propionitriles of our invention for their organoleptic utilities.

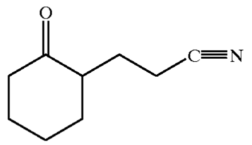

is known for use in perfumery as disclosed in Japanese Published Application No. JP60/151440 (Sumitomo). The synthesis of this material is also disclosed by Cotarca, et al, *SYNTHESIS,* 1996, pages 328–332.

The nitrile having the structure:

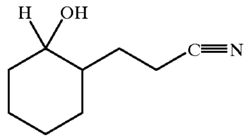

is disclosed in the prior art, but not for its perfumery uses by Dynamit Nobel AG in German Patent No. 1,912,790 (1970). Its preparation is set forth by Duféÿ, *BULLETIN DE LA SOCIÉTÉ CHIMIQUE DE FRANCE,* 1968, No. 11.

The compounds having the structure:

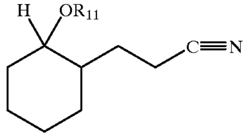

wherein $R_{11}$ is methyl or ethyl are disclosed by Giese, et al, *Chem. Ber.,* 117 (1984) 6, pages 2120–2139, but their organoleptic utilities are not disclosed.

The compound having the structure:

The compound having the structure:

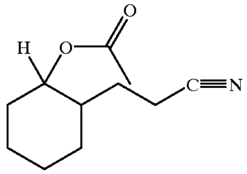

is disclosed by Tureček, Collection Czechoslovak Chem. Commun. (1982), Vol. 47 (3), pages 858–876, but its organoleptic uses are not disclosed or inferred.

Nothing in the prior art discloses any organoleptic uses of the compounds having the structure:

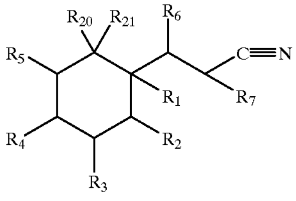

wherein $R_{20}$ and $R_{21}$ are the same or different $C_1$–$C_4$ lower alkoxy; or wherein $R_{20}$ is hydrogen and $R_{21}$ is hydroxy, $C_1$–$C_3$ lower alkoxy or $C_1$–$C_3$ lower acyloxy; and wherein $R_1$, $R_2$, $R_3$, $R_4$, $R_5$, $R_6$ and $R_7$ are the same or different hydrogen or $C_1$–$C_4$ lower alkly.

Furthermore, the prior art does not disclose the compounds having the structure:

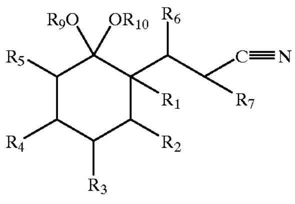

wherein $R_9$ and $R_{10}$ are $C_1$–$C_4$ lower alkyl.

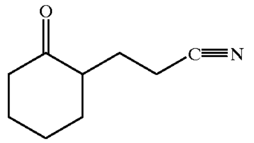

(conditions: 50 meter×0.32 mm bonded fused silica/methyl silicone column programmed from 75 up to 250° C. at 2° C. per minute).

Figure 1:
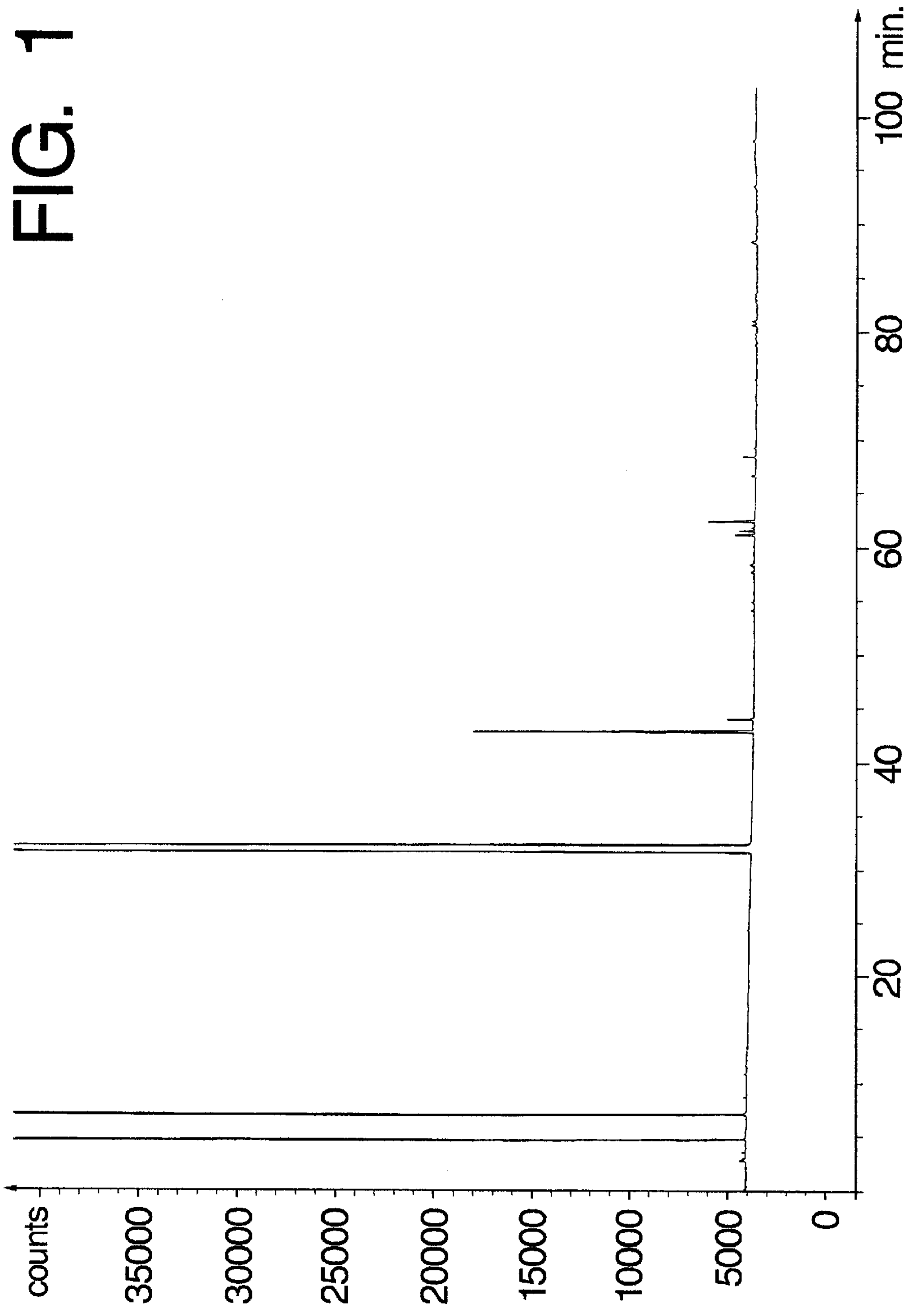
FIG. 1 is a GC capillary column survey for the reaction product of Example I containing the compound having the structure.
Figure 2:
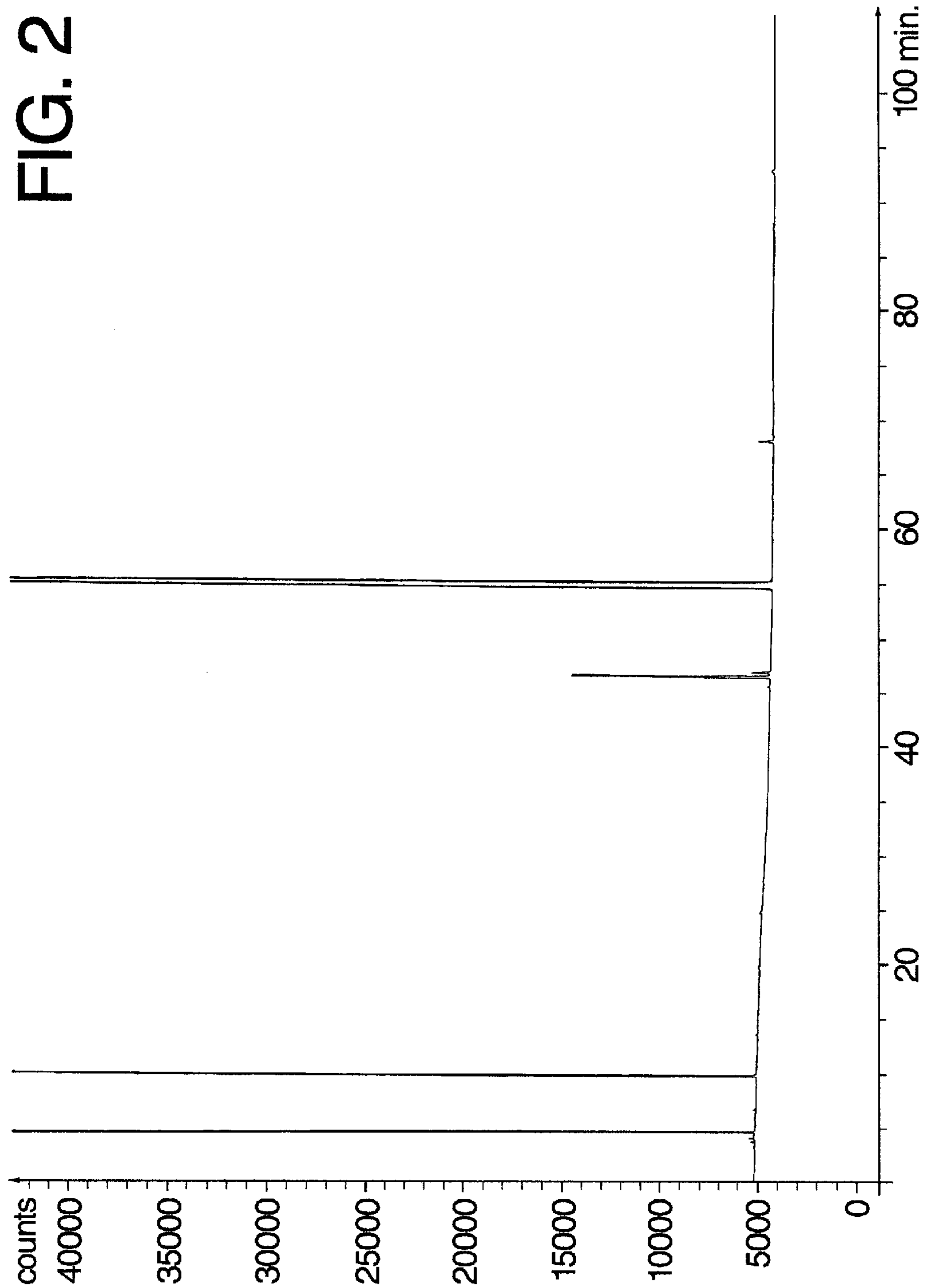

FIG. 2 is a GC capillary column survey for the reaction product of Example I containing the compound having the structure:

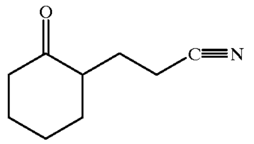

(conditions: 50 meter×0.32 mm Carbowax 20M/fused silica column programmed from 75 up to 250° C. at 2° C. per minute).

Figure 3:
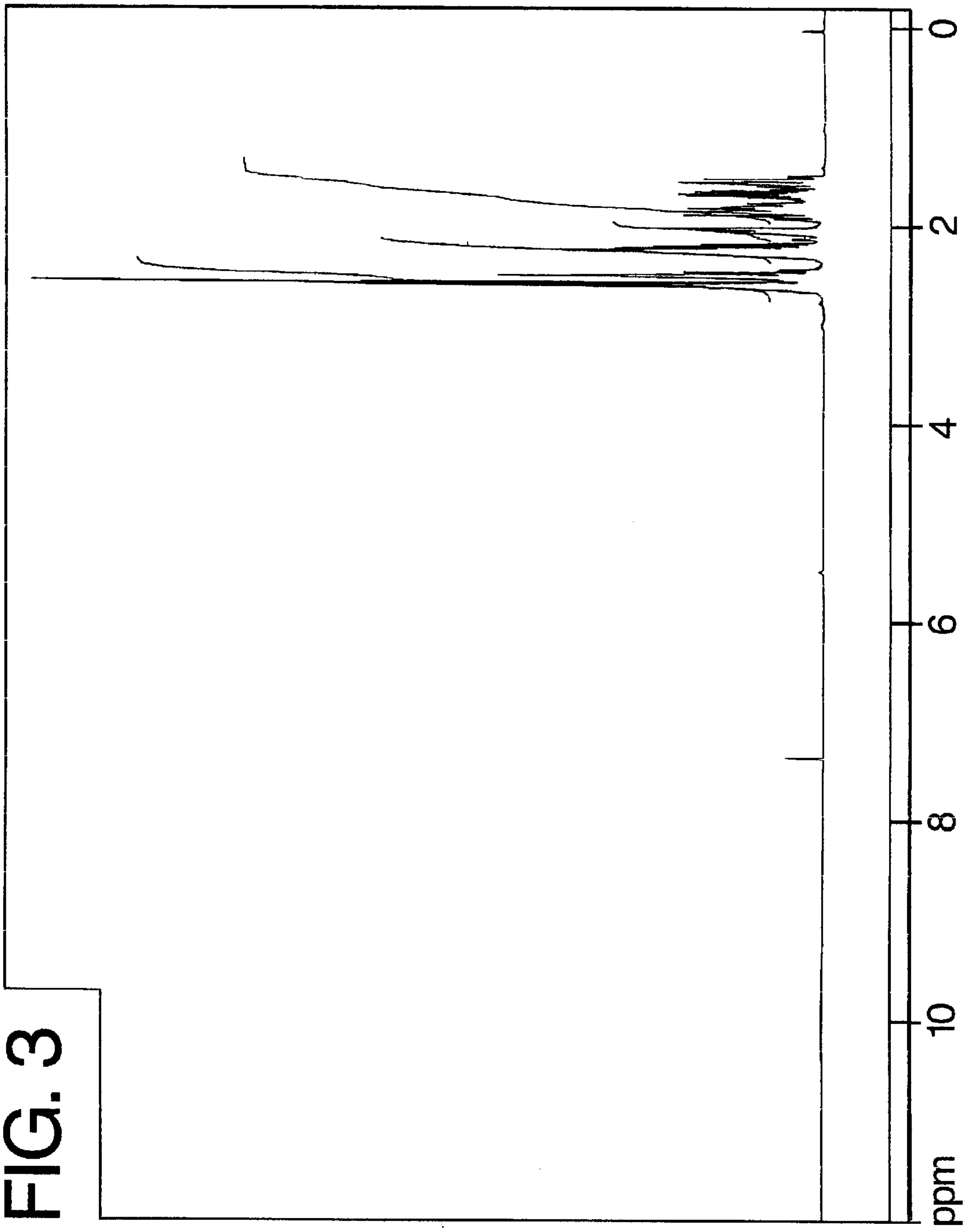

FIG. 3 is the NMR spectrum for the compound having the structure:

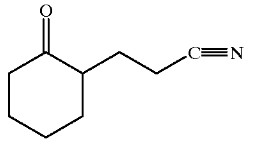

prepared according to Example I.

FIG. 4A is a GC capillary column survey for the reaction product of Example II containing the compound having the structure:

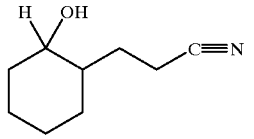

(conditions: 50 meter×0.32 mm bonded fused silica/methyl silicone column programmed from 75° C. up to 250° C. at 2° C. per minute).

FIG. 4B is a GC capillary column survey for the reaction product of Example II containing the compound having the structure:

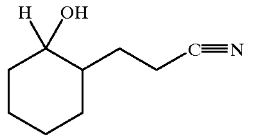

(conditions: 50 meter×0.32 mm fused silica/Carbowax 20M column programmed from 75° C. up to 250° C. at 2° C. per minute).

Figure 5:
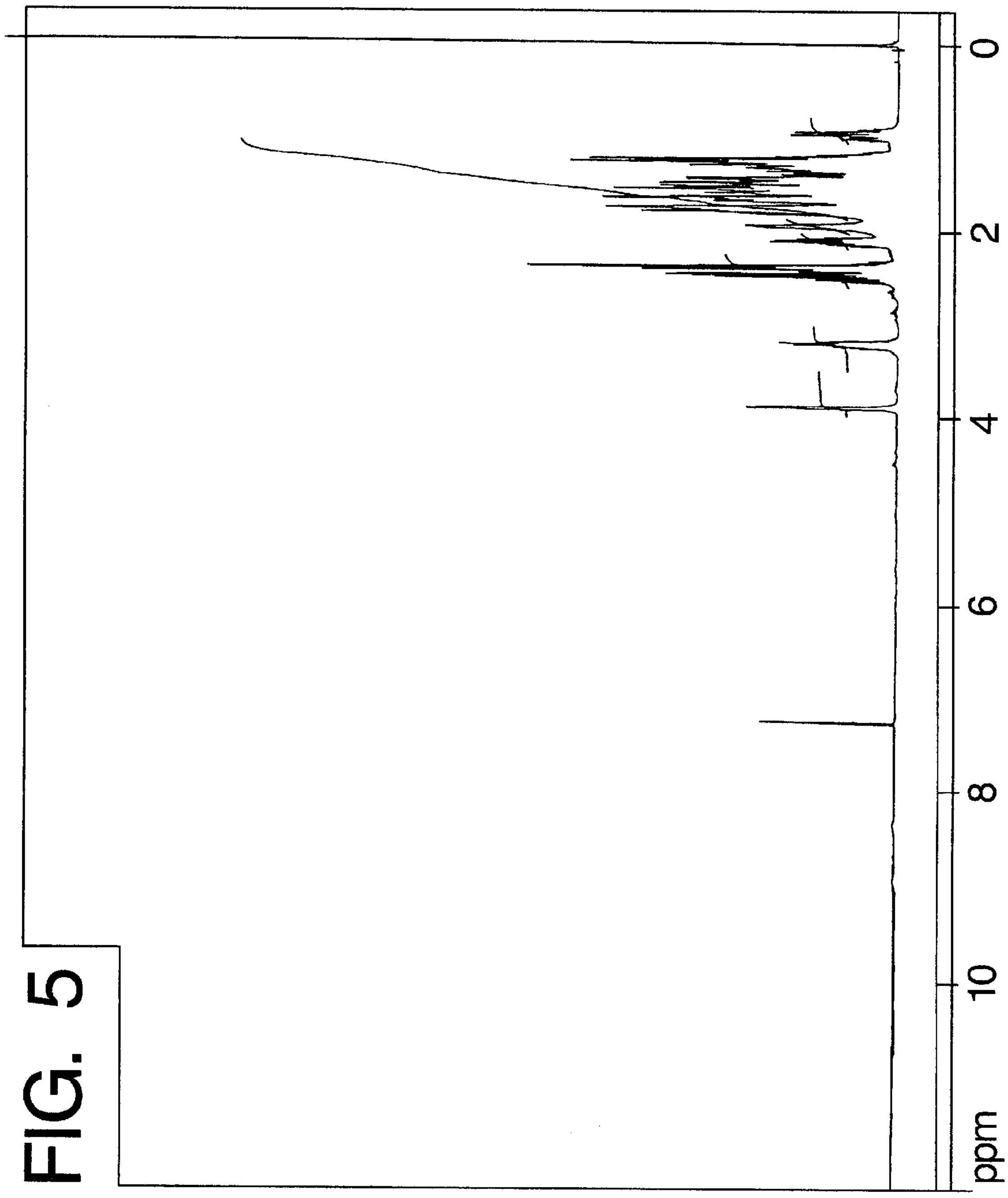

FIG. 5 is the NMR spectrum for the compound having the structure:

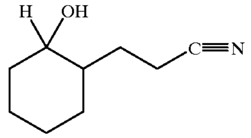

prepared according to Example II.

Figure 6:
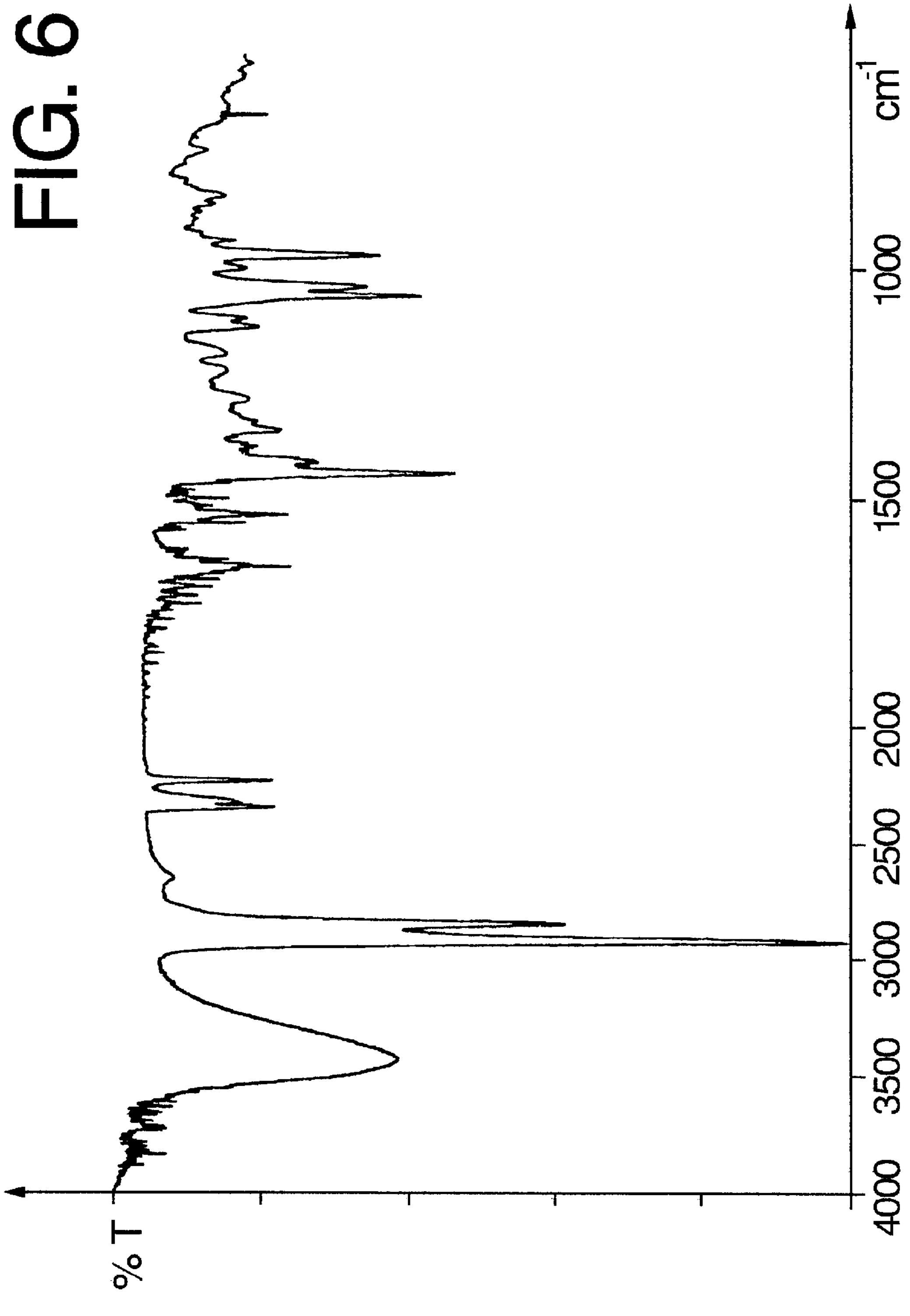

FIG. 6 is the infrared spectrum for the compound having the structure:

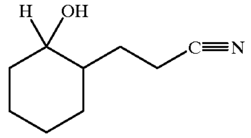

prepared according to Example II.

FIG. 7A is a GC capillary column survey of the reaction product of Example III containing the compound having the structure:

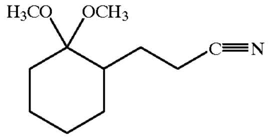

(conditions: 50 meter×0.32 mm bonded fused silica/methyl silicone column programmed from 75° C. up to 250° C. at 2° C. per minute).

FIG. 7B is a GC capillary column survey for the reaction product of Example III containing the compound having the structure:

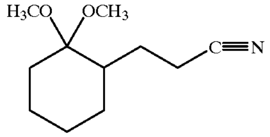

(conditions: 50 meter×0.32 mm fused silica/Carbowax 20M column programmed from 75° C. up to 250° C. at 2° C. per minute).

Figure 8:
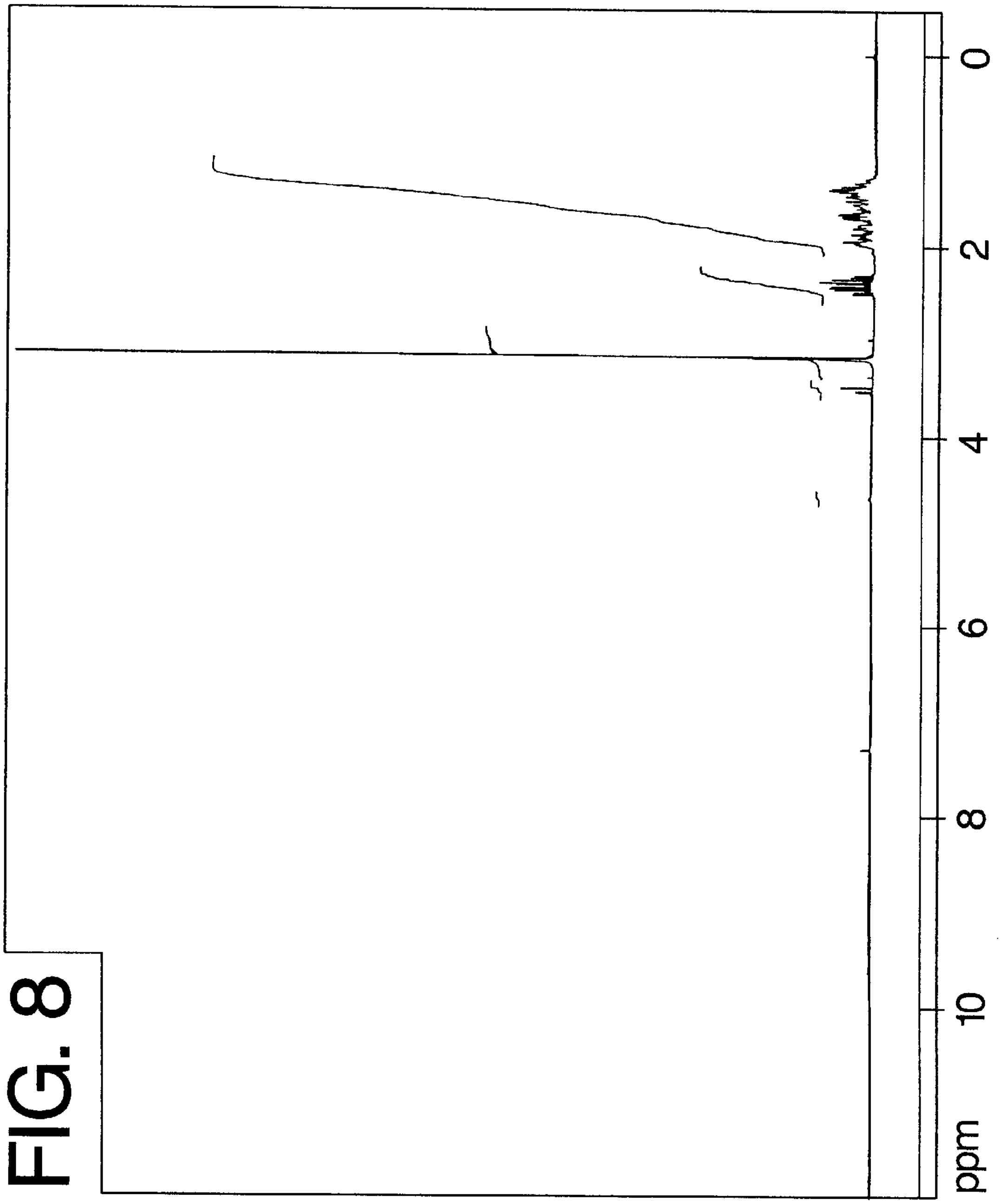

FIG. 8 is an NMR spectrum for the compound having the structure:

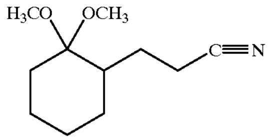

prepared according to Example III.

Figure 9:
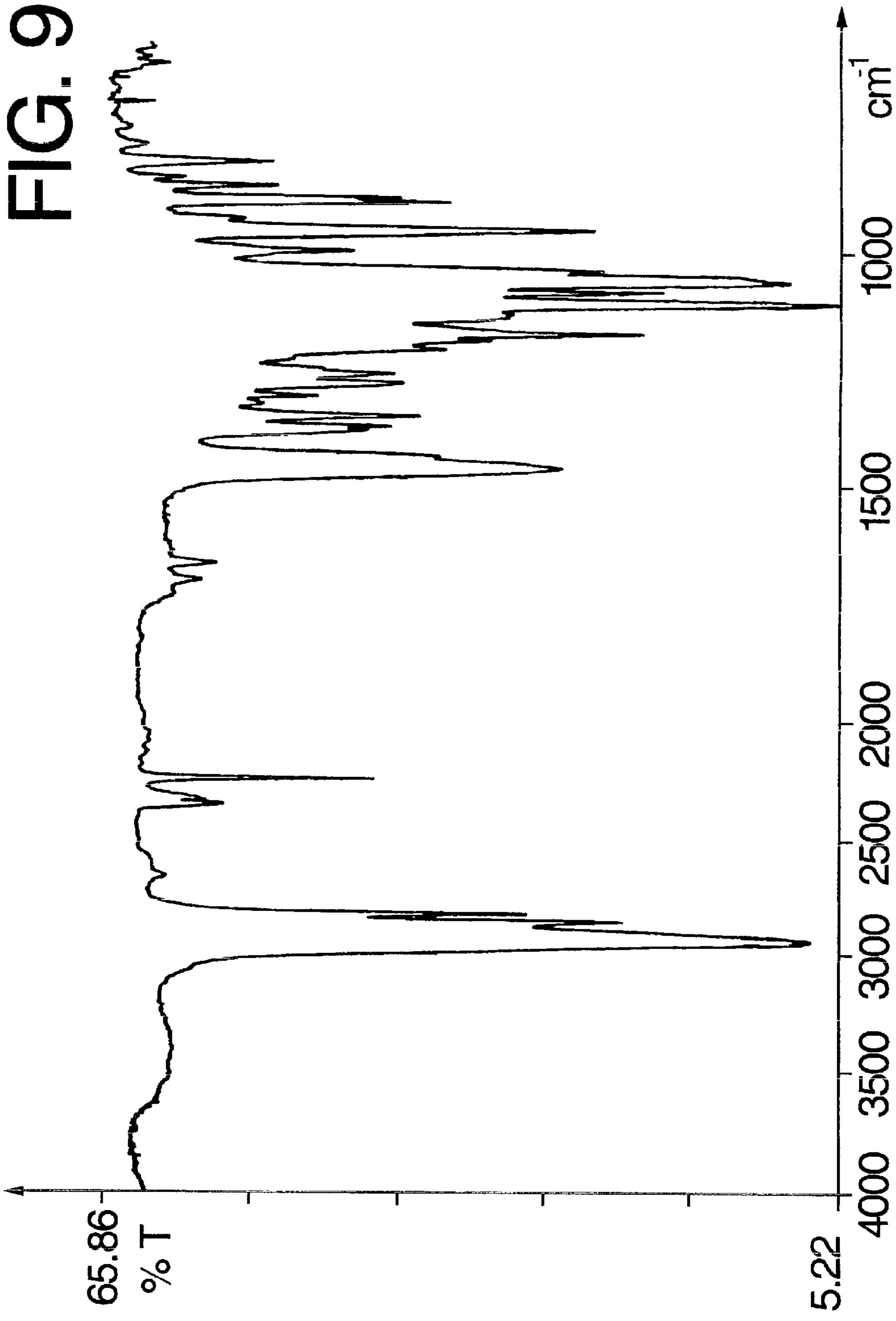

FIG. 9 is an infrared spectrum for the compound having the structure:

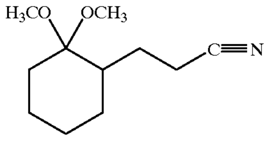

prepared according to Example III.

FIG. 10 is a partial side elevation and partial sectional view of an apparatus for forming polymer pellets scented with one of the perfume compositions or perfumery materials of our invention containing at least one of the α-oxygen-substituted cyclohexane propionitriles of our invention.

FIG. 11 is a section taken on line 11—11 of FIG. 10.

DETAILED DESCRIPTION OF THE DRAWINGS

Referring to FIGS. 10 and 11, the apparatus used in producing polymeric fragrances containing at least one of the α-oxygen-substituted cyclohexane propionitriles of our invention comprises a device for forming scented polyolefin (for example) pellets which comprises a vat or container 212 into which a mixture of polyolefins such as polyethylene or an aromatic substance or scented material containing or consisting of at least one of the α-oxygen-substituted cyclohexane propionitriles of our invention is placed. The container is closed by an airtight lid 228 and clamped to the container by bolts 265. A stirrer 273 traverses the lid or cover 228 in an airtight manner and is rotated in a suitable manner. A surrounding cylinder 212 having heating coils which are supplied with electric current through cable 224 from a rheostat or control 216 is operated to maintain the temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 220–280° F. The heater 212A is operated to maintain the upper portion of the container 212 within a temperature range of from 250–350° F. The bottom portion of the container 212 is heated by means of heating coils 212A heated through a control 220 connected thereto through a connecting wire 226 to maintain the lower portion of the container 212 within a temperature range of from 250–350° F.

Thus, polymer (e.g., polyethylene) added to the container 212 is heated from 10–12 hours whereafter a scent or aroma-imparting material which contains or consists of at least one of the α-oxygen-substituted cyclohexane propionitriles of our invention is quickly added to the melt. The material must be compatible with the polyolefin and forms a homogeneous liquid melt therewith. The scented material containing or consisting of at least one of the α-oxygen-substituted cyclohexane propionitriles of our invention is of a type for the particular aroma desired and formulated specifically for the scenting purpose for which the polyolefin will be employed. Aromatic materials, in some instances in solid or powdered form, may be employed or added to the polyolefin in the container 212. Generally, about 10–30% by weight of the scenting material is added to the polyolefin.

After the scent-imparting material containing or consisting of at least one of the α-oxygen-substituted cyclohexane propionitriles of our invention is added to the container 212, the mixture is stirred for a few minutes, for example, 5–15 minutes, and maintained within the temperature ranges indicated previously by the heating coils 212A. The controls 216 and 220 are connected through cables 224 and 226 to a suitable supply of electric current for supplying the power for heating purposes. The controls 216 and 220 are connected to the heating coils 212A, respectively, through wires 214 and 222.

Thereafter, the valve "V" is opened permitting the mass to flow outwardly through conduit 232 (also indicated by reference numeral 218 in FIG. 10) having a multiplicity of orifices 234 adjacent to the lower side thereof. The outer end of the conduit 232 is closed so that the liquid polymer (e.g., polyethylene), which contains an aroma-imparting mixture (containing at least one of the α-oxygen-substituted cyclohexane propionitriles of our invention) will continuously drop through the orifices 234 downwardly from the conduit 232. During this time, the temperature of the polymer (e.g., polyethylene) containing the aroma mixture containing at least one of the α-oxygen-substituted cyclohexane propionitriles of our invention in the container 212 is accurately controlled so that a temperature in the range of from 210–275° F. will exist in the conduit 232. The regulation of the temperature through the control 220 and the control 216 is essential in order to insure temperature balance to provide for the continuous dropping or dripping of molten polymer (e.g., polyethylene) in combination with scenting material containing or consisting of at least one of the α-oxygen-substituted cyclohexane propionitriles of our invention through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with chilled water or some other suitable cooling liquid (which will not dissolve the pellets) in order to insure the rapid cooling of each of the pellets and maintenance of said pellets in the solid phase. The pellets 244 are then collected from the container 245 and utilized in a process as illustrated, infra.

A feature of this aspect of the process of our invention is in the provision for moistening the conveyor belt 238 in order to insure rapid formation of the solid polymer—(e.g., polyethylene) scented pellets 244 without sticking to the belt 238. The belt 238 is advantageously constructed of a material which will not normally stick to a melted polymer, but the moistening means 248 insures a sufficiently cold temperature of the belt surface for the adequate formation of the solid phase pellets 244. The moistening means comprises a container 250 which is continuously fed with water 254 to maintain a level for moistening a sponge element 256 which bears against the exterior of the conveyor belt 238 while the conveyor belt is in motion.

THE INVENTION

The instant invention provides α-oxygen-substituted cyclohexane propionitriles defined according to the generic structure:

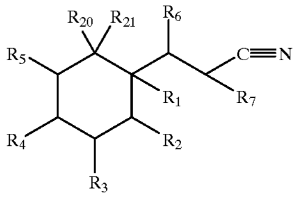

wherein $R_{20}$ and $R_{21}$ are the same or different $C_1$–$C_4$ lower alkoxy; or wherein $R_{20}$ is hydrogen and $R_{21}$ is hydroxy, $C_1$–$C_3$ lower alkoxy or $C_1$–$C_3$ lower acyloxy; and wherein $R_1$, $R_2$, $R_3$, $R_4$, $R_5$, $R_6$ and $R_7$ are the same or different hydrogen or $C_1$–$C_4$ lower alkyl.

The α-oxygen-substituted cyclohexane propionitriles of our invention as defined, supra, impart, augment and/or enhance woody, orris, sweet and coumarinic aromas with spicy and soft floral undertones in or to perfume compositions, colognes and perfumed articles (e.g., solid or liquid anionic, cationic, nonionic or zwitterionic detergents, perfumed polymers, fabric softener compositions, fabric softener articles, hair care compositions, cosmetic powders and the like).

Briefly, the α-oxygen-substituted cyclohexane propionitriles of our invention may be prepared by first reacting at least one compound defined according to the structure:

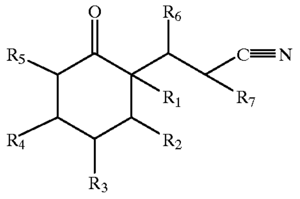

with an acrylonitrile derivative defined according to the structure:

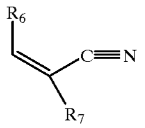

(wherein $R_1$, $R_2$, $R_3$, $R_4$, $R_5$, $R_6$ and $R_7$ are as defined, supra) in accordance with the reaction:

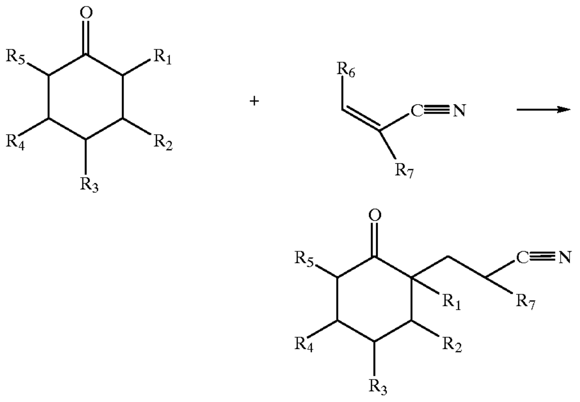

under such conditions as set forth in U.S. Pat. No. 3,816,503 issued on Jun. 11, 1974 (the specification for which is incorporated by reference herein) or under such conditions as set forth in U.S. Pat. No. 5,917,067 issued on Jun. 29, 1999 (the specification for which is incorporated by reference herein) or under such conditions as set forth in Published PCT Application No. 94/29258 published on Dec. 22, 1994 (the specification for which is incorporated by reference herein).

An example of the aforementioned reaction using pyrrolidine to form the intermediary enamine is shown as follows:

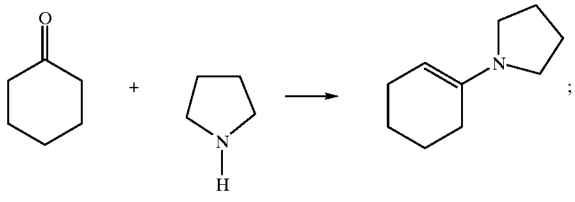
;

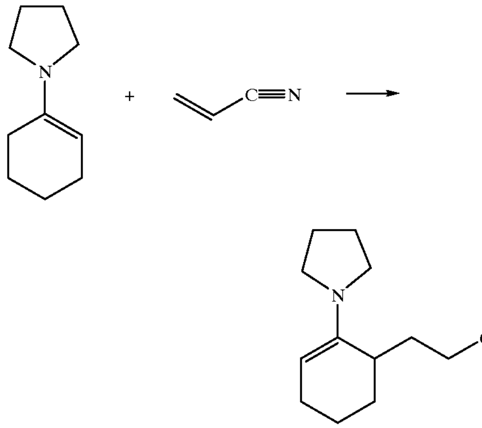
; and

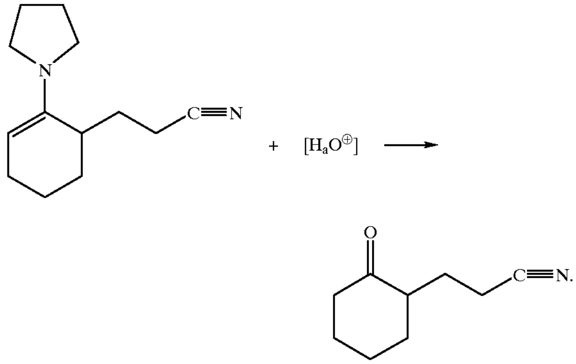
.

This reaction sequence is shown summarily as follows:

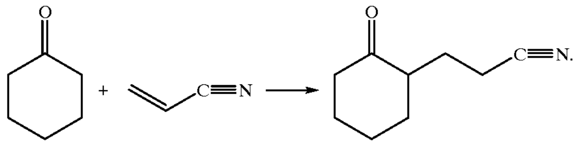
.

The resulting product defined according to the structure:

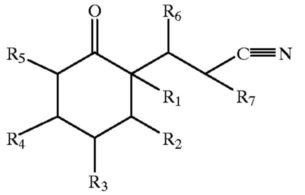

may then be reduced or ketalized in order to form compounds useful in the practice of our invention, that is, the α-oxygen-substituted cyclohexane propionitriles of our invention.

Thus, the resulting ketones defined according to the structure:

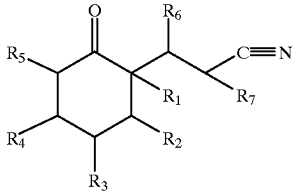

may be reduced using a reducing agent such as an alkali metal borohydride according to the reaction:

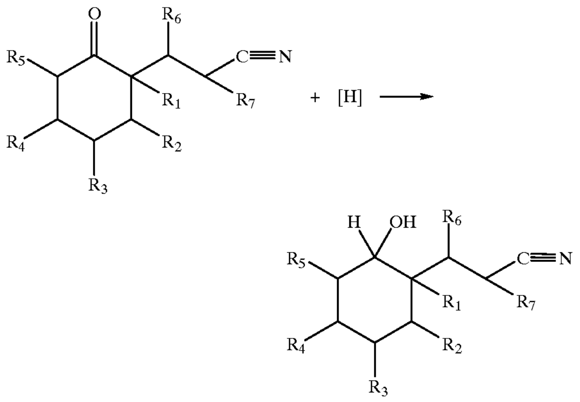

and the resulting secondary alcohol having the structure:

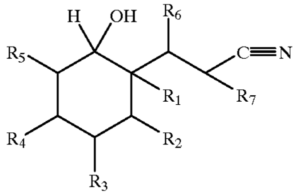

may be used "as-is" or the resulting secondary alcohol having the structure:

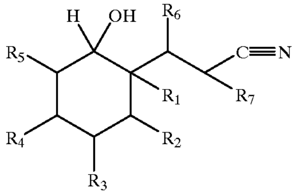

may be further reacted to form esters or ethers.

Such esters or ethers having the generic structure:

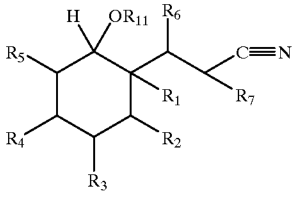

wherein $R_{11}$ represents $C_1$–$C_3$ acyl or alkyl are formed according to the reaction:

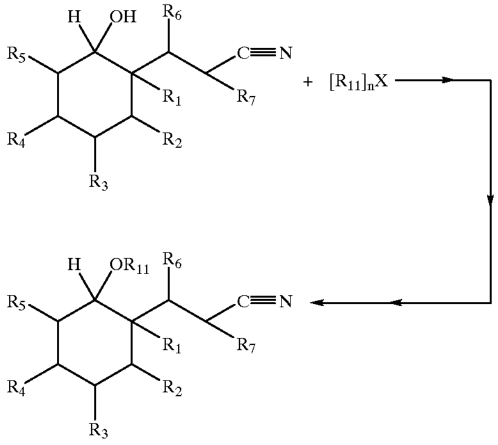

using the reagent defined according to the structure:

$[R_{11}]_nX$, wherein n is 1 or 2 and

X is chloro, bromo or iodo when n is 1 and X is oxygen when n is 2 and $R_{11}$ is acyl; and X is sulfate when n is 2 and $R_{11}$ is $C_1$–$C_3$ alkyl. Thus, for example a reduction reaction is as follows:

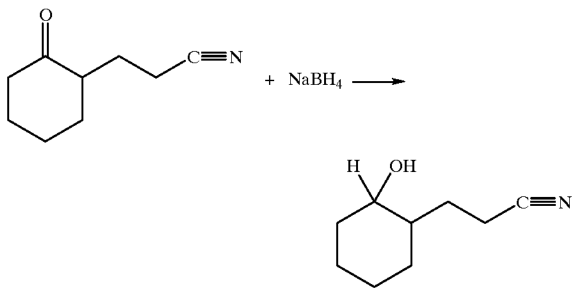

and is carried out using the conditions as taught by Duféÿ, *BULLETIN DE LA SOCIÉTÉ CHIMIQUE DE*

*FRANCE,* 1968, No. 11, pages 4653–4662, incorporated herein by reference and exemplified in Example II, infra.

By way of further example, the resulting reduced product may be etherified or acylated to form ethers or esters according to the reaction:

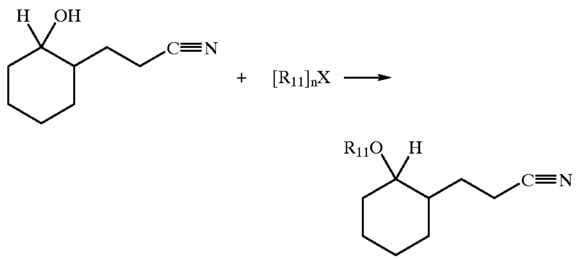

or, more specifically, by means of the reactions:

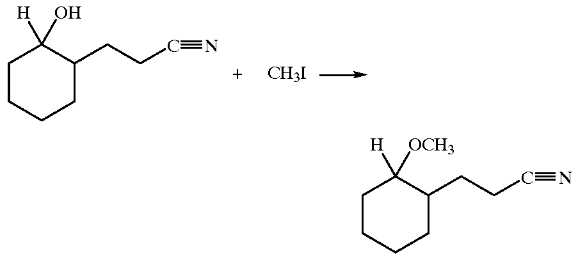

(to form a methyl ether) or:

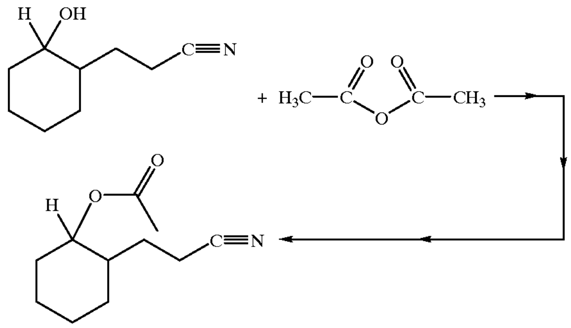

(to form an acetate ester).

The conditions for the ether formation are set forth, for example, in *Chem. Ber., Volume* 117, pages 2132–2139 (1984), B. Giese, et al, published on Aug. 17, 1983 and incorporated by reference herein.

Specifically for the formation of alkyl ethers, the reaction:

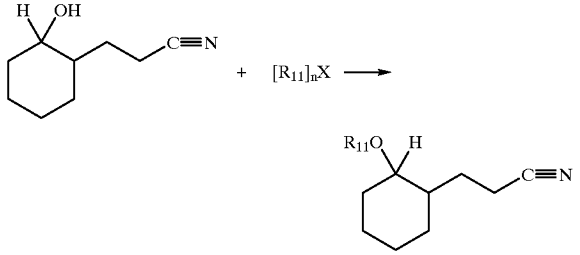

can be carried out wherein X is chloro, bromo, iodo or sulfate; n is 1 or 2; and $R_{11}$ is lower alkyl with the proviso that n is 1 when X is chloro, bromo or iodo and n is 2 when X is sulfate. An example of such a reaction to form ethers is the following:

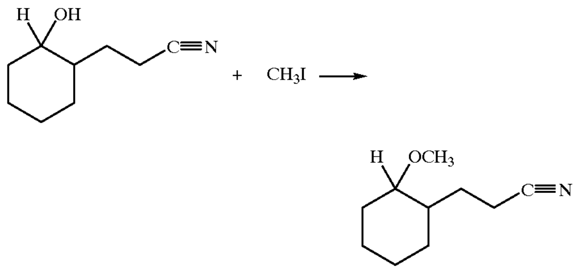

In forming esters useful in the practice of our invention, the following reaction can take place as an example:

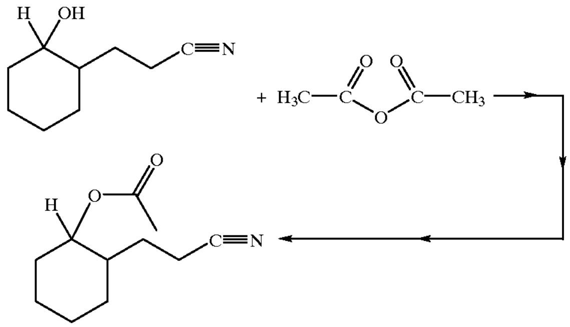

in order to form the resulting acetate.

As stated, supra, these reactions take place under conditions well known to those having ordinary skill in the art, for example, using the procedures taught by Tureček, *Collection Czechoslovak Chem. Commun.,* Volume 47 (1982), pages 858–876 and entitled "PREPARATION OF 7-OXABICYCLO[4.3.0]NONANES AND 2-OXABICYCLO[4.4.01]DECANES SPECIFICALLY LABELLED WITH DEUTERIUM."

Ketals of our invention defined according to the structure:

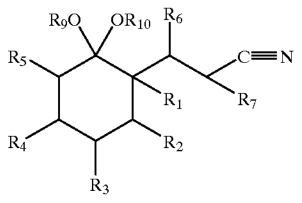

wherein $R_9$ and $R_{10}$ are the same or different and each represents $C_1$–$C_4$ lower alkyl may be produced according to the reaction:

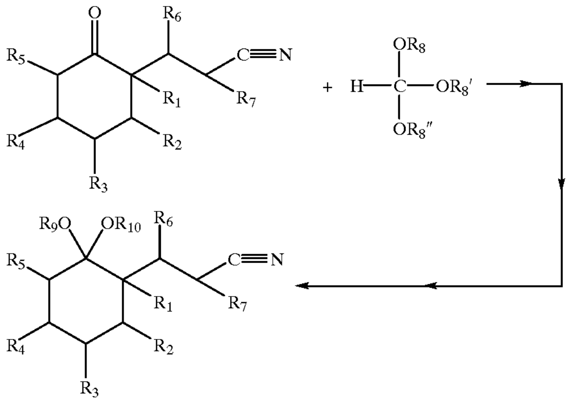

wherein $R_8$, $R_8'$ and $R_8''$ are the same or different $C_1$–$C_4$ lower alkyl. Thus, when $R_9$ and $R_{10}$ are different then differences exist as between $R_8$, $R_8'$ and $R_8''$. Thus, the reaction takes place between a trialkyl orthoformate defined according to the structure:

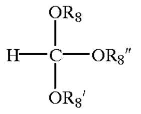

and a ketocyclohexylpropionitrile having the structure:

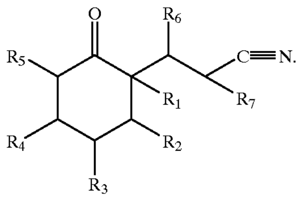

The mole ratio of trialkyl orthoformate:nitrile derivative may vary from about 0.5:1 up to about 1.5:1 with a preferred excess of trialkyl orthoformate in the reaction mass. The reaction temperature may vary from about 15° C. up to about 30° C. and the reaction pressure may vary from about 1 atmosphere up to about 10 atmospheres.

The reaction takes place in the presence of an inert solvent such as a lower alkanol preferably wherein the lower alkanol has the same alkyl moiety as the trialkyl orthoformate. The weight ratio of solvent:reaction mass may vary from about 1:5 up to about 1:10. The reaction takes place in the presence of a very low concentration of acid wherein the concentration of acid in the reaction mass may vary from about 0.5 grams/liter up to about 2 grams/liter. The reaction time may vary from about 0.1 hour up to about 2 hours.

At the end of the reaction, the reaction mass is washed with weak base and then dried over an anhydrous salt such as anhydrous sodium bicarbonate. The resulting product is fractionally distilled. An example of such a reaction is:

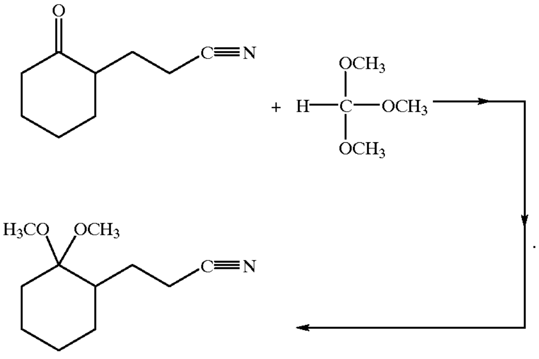

In such a reaction, byproducts are formed as defined according to the structure:

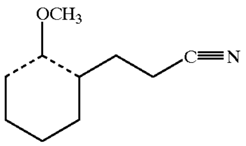

wherein one of the dashed lines is a carbon carbon double bond and the other of the dashed lines is a carbon carbon single bond, to wit:

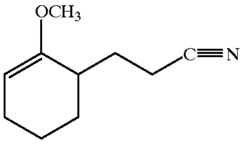

and

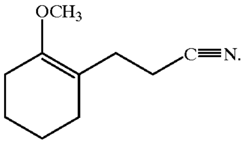

At most, the amount of compounds having the structure:

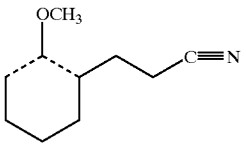

formed is approximately 5% by weight of the entire product formed.

In carrying out the foregoing reactions, it is to be understood that various stereoisomers are formed, for example, those having the structures:

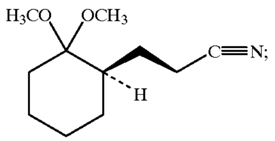

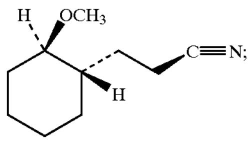

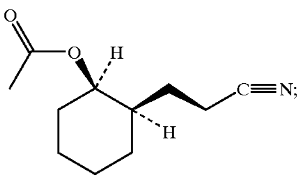

-continued

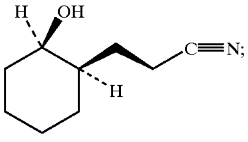

and

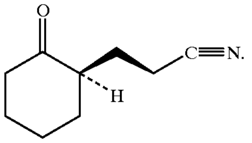

The following table sets forth examples of compounds produced according to the processes of our invention and their organoleptic properties:

TABLE I

| Compound | Organoleptic Property |
|---|---|
| The compound having the structure: 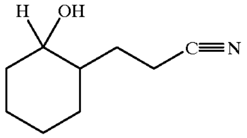 | A sweet, coumarinic aroma with soft floral (muguet) undertones. |
| The compound having the structure: 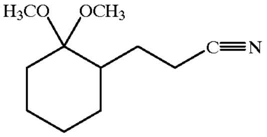 | A woody, orris aroma with spicy undertones. |

The compounds defined according to the generic structure:

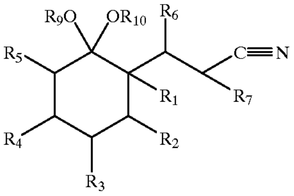

are novel compounds. This generic structure includes the compound having the structure:

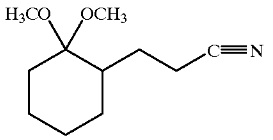

as well as the stereoisomer having the structure:

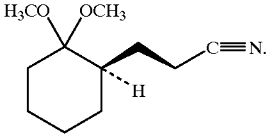

At least one of the α-oxygen-substituted cyclohexane propionitriles of our invention and one or more auxiliary perfume ingredients including, for example, alcohols (other than the alcohols of our invention), aldehydes, ketones (other than the ketones of our invention), terpenic hydrocarbons, esters (other than the esters of our invention), lactones, ethers (other than the ethers of our invention), natural essential oils and synthetic essential oils may be admixed so that the combined odors of the individual components produce a pleasant and desired fragrance, particularly and preferably in the floral and piney fragrance area. Such perfume compositions usually contain (a) the main note or the “bouquet” or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, at least one of the α-oxygen-substituted cyclohexane propionitriles of our invention can be used to alter, modify or enhance the aroma characteristics of a perfume composition, for example, by utilizing or moderating the olfactory reaction contributed by another ingredient in the composition.

The amount of one or more of the α-oxygen-substituted cyclohexane propionitriles of our invention which will be effective in the perfume composition as well as in the perfumed articles and colognes of our invention depends on many factors including the other ingredients, their amounts and the effects which are desired. It has been found that perfume compositions containing as little as 0.01% of at least one of the α-oxygen-substituted cyclohexane propionitriles of our invention or even less (e.g., 0.005%) can be used to impart, augment or enhance woody, orris, sweet, coumarinic aromas with spicy, soft floral (muguet) undertones in and to soaps, cosmetics, solid or liquid anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought.

One or more of the α-oxygen-substituted cyclohexane propionitriles of our invention are useful (taken alone or together with other ingredients in the perfume composition) as (an) olfactory component(s) in detergents and soaps, space odorants and deodorants, perfumes, colognes, toilet water, bath preparations such as creams, deodorants, hand lotions and sun screens; powders such as talcs, dusting powders, face powders and the like. When used as (an) olfactory component(s), as little as 1% of at least one of the α-oxygen-substituted cyclohexane propionitriles of our invention or even less will suffice to impart intense and substantive woody, orris, sweet, coumarinic aromas with spicy, soft floral (muguet) undertones to floral and piney formulations. Generally, no more than 20% of at least one of the α-oxygen-substituted cyclohexane propionitriles of our invention based on the ultimate end product is required in the perfume composition.

Accordingly, in the perfume compositions and colognes, from about 0.01% up to about 70% of the perfume composition may be at least one of the α-oxygen-substituted cyclohexane propionitiles of our invention. In perfumed articles, the quantity of at least one of the α-oxygen-substituted cyclohexane propionitriles of our invention may vary from about 0.005% up to about 25% of the perfumed article; and up to about 8% in the case of solid or liquid anionic, cationic, nonionic or zwitterionic detergents, for example.

In addition, the perfume composition or fragrance composition of our invention can contain a vehicle or carrier for at least one of the α-oxygen-substituted cyclohexane propionitriles of our invention. The vehicle can be a liquid such as a nontoxic alcohol such as ethyl alcohol or a nontoxic glycol such as propylene glycol or the like. The carrier can also be an absorbent solid such as a gum (e.g., gum arabic, xanthan gum or guar gum or mixtures of same) or components for encapsulating the composition (such as gelatin as by means of coacervation or such as a urea-formaldehyde prepolymer when a polymeric wall is intended to be formed around a liquid perfume composition center).

The following Examples I–III serve to illustrate the processes for preparing the compounds useful in the practice of our invention and the compounds useful for their organoleptic properties. Examples following Example III (Example IV, et seq.) illustrate organoleptic utilities of the α-oxygen-substituted cyclohexane propionitriles of our invention.

All parts and percentages given herein are by weight unless otherwise specified.

EXAMPLE I

Preparation of 3-(α-ketocyclohexyl)propionitrile

Reactions

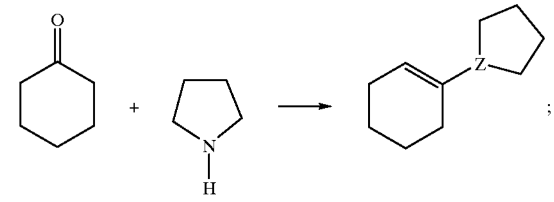

;

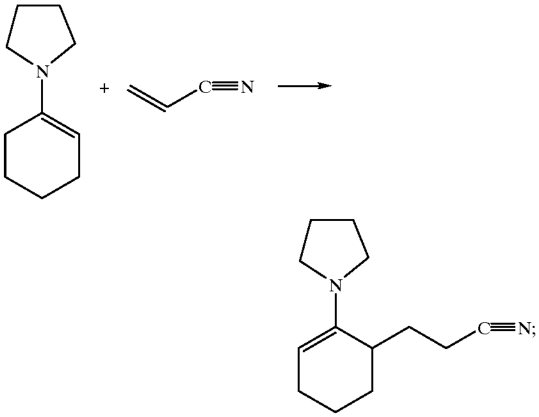

and

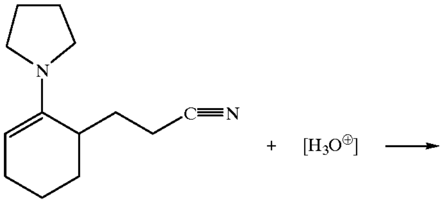

-continued

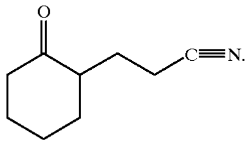

(Summary of reactions:

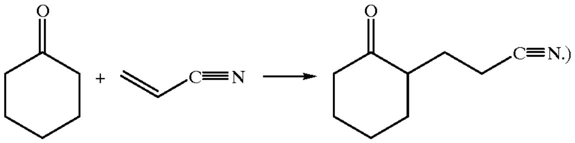

Into a 1 liter reaction vessel equipped with reflux condenser/Bidwell water removal apparatus, thermometer, heating mantle and addition funnel are placed 490 grams of cyclohexenone and 36 grams of pyrrolidine. The reaction mass is heated to reflux with stirring and water is removed via the Bidwell apparatus. After 1 hour, the reaction mass is cooled to 110–115° C. and over a period of 0.5 hours, 235 grams of acrylonitrile having the structure:

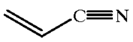

is added to the reaction mass.

The reaction mass is then heated with stirring for a period of 2 hours at a temperature of 125° C. At the end of the 2 hour period, the reaction mass is cooled and it is combined with an equal volume of 10% hydrochloric acid. The reaction mass is then washed with toluene and the toluene extract is separated and admixed with saturated aqueous sodium carbonate. The reaction mass is then distilled at a temperature in the range of 113–116° C. at 4 mm/Hg pressure to yield the compound having the structure:

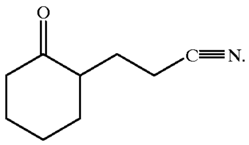

EXAMPLE II

Preparation of 3(2-hydroxycyclohexyl)propionitrile

Reaction

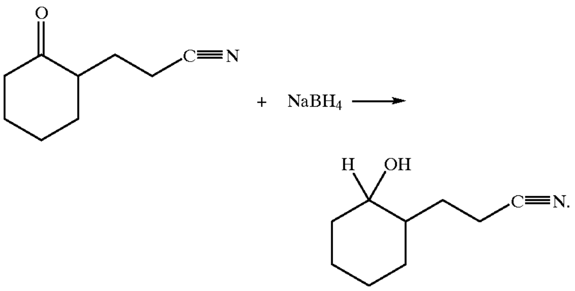

Into a 3 liter reaction vessel equipped with stirrer, thermometer, reflux condenser and heating mantle are placed 1,500 ml of isopropyl alcohol and 42 grams of sodium borohydride. With stirring, the resulting mixture is heated to 60° C. and maintained at 60–80° C. Over a period of 1 hour, 570 grams of the compound having the structure:

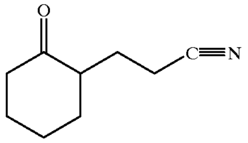

prepared according to Example I, supra, is added to the reaction mass.

The reaction mass is then maintained at 50° C. for a period of 1 hour.

The reaction mass is then transferred to a 10 liter vessel and a 50:50 water/acetic acid mixture (equal volume) is added to the reaction mass. The reaction mass is then heated to 80–100° C. while simultaneously distilling the isopropyl alcohol solvent.

The reaction mass is then washed with an equal volume of a 5% aqueous solution of sodium hydroxide at 50° C.

The organic phase is separated from the aqueous phase and the organic phase is fractionally distilled yielding the following fractions:

| Fraction No. | Vapor Temperature | Liquid Temperature | Vacuum mm/Hg | Reflux Ratio |
|---|---|---|---|---|
| 1 | 23/37 | 23/110 | 120/20 | 100:1 |
| 2 | 127 | 152 | 21 | 4:1 |
| 3 | 133 | 158 | 21 | 4:1 |
| 4 | 132 | 158 | 21 | 4:1 |
| 5 | 133 | 159 | 21 | 4:1 |
| 6 | 133 | 158 | 21 | 4:1 |
| 7 | 132 | 158 | 21 | 4:1 |
| 8 | 133 | 159 | 21 | 4:1 |
| 9 | 132 | 158 | 21 | 4:1 |
| 10 | 134 | 160 | 21 | 4:1 |
| 11 | 134 | 160 | 21 | 4:1 |
| 12 | 133 | 163 | 21 | 4:1 |
| 13 | 135 | 165 | 21 | 4:1 |
| 14 | 120 | 190 | 21 | 4:1 |

Fraction numbers 4–12 are bulked and the bulked distillation fractions are then used "as is" for their organoleptic properties as indicated, infra, for farther reacted to form alkyl ethers or esters of our invention.

NMR, IR and mass spectral analyses confirm the resulting product as having the structure:

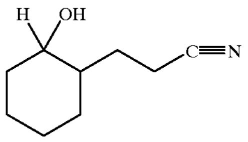

including the stereoisomer having the structure:

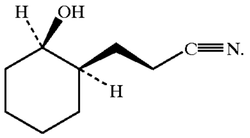

The compound having the structure:

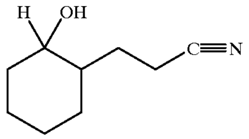

produced according to this example has a sweet, coumarinic aroma with soft floral (muguet) undertones.

EXAMPLE III

Preparation of 3(2,2-dimethoxycyclohexyl)propionitrile

Reaction

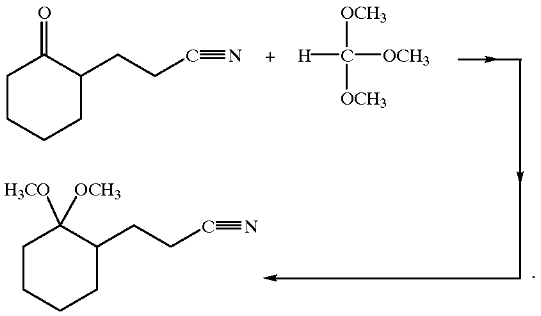

Into a 1 liter reaction vessel equipped with stirrer, thermometer, reflux condenser, heating mantle and addition funnel are placed 302 grams (2.0 moles) of the compound having the structure:

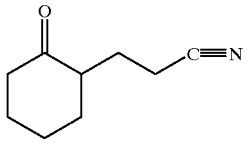

prepared according to Example I and 292 grams of trimethyl orthoformate having the structure:

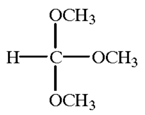

(2.75 moles) and, in addition, 50 ml of anhydrous methyl alcohol.

With stirring, the resulting mixture is cooled to −10° C. and maintained at −10° C. for a period of 1 hour.

One ml of 3 molar hydrochloric acid is then added to the reaction mass and the reaction mass is allowed to warm to 15–20° C. over a period of 1 hour.

At the end of the 1 hour period, GLC analysis together with NMR analysis indicates that the reaction is complete.

The reaction mass is then admixed with an equal volume of aqueous saturated sodium acetate solution.

The organic phase is separated from the aqueous phase and the organic phase is washed with an equal volume of 10% aqueous sodium bicarbonate solution.

The resulting product is dried over anhydrous magnesium sulfate and fractionally distilled yielding the following fractions:

| Fraction No. | Vapor Temperature | Liquid Temperature | Vacuum mm/Hg | Reflux Ratio |
|---|---|---|---|---|
| 1 | 23/31 | 23/11.5 | 150/15 | 100:1 |
| 2 | 111 | 140 | 1 | 4:1 |
| 3 | 114 | 140 | 1 | 4:1 |
| 4 | 117 | 140 | 1 | 4:1 |
| 5 | 118 | 140 | 1 | 4:1 |
| 6 | 118 | 140 | 1 | 4:1 |
| 7 | 119 | 140 | 1 | 4:1 |
| 8 | 112 | 141 | 1 | 4:1 |
| 9 | 120 | 140 | 1 | 4:1 |
| 10 | 119 | 141 | 1 | 4:1 |
| 11 | 119 | 140 | 1 | 4:1 |
| 12 | 120 | 152 | 1 | 4:1 |
| 13 | 120 | 152 | 1 | 4:1 |
| 14 | 56 | 184 | 1 | 4:1 |

Fractions 3–11 are bulked and the bulked distillation fractions have an intense and substantive woody and orris aroma with spicy undertones.

The resulting product as confirmed by NMR, IR, GLC and mass spectral analyses has the structure:

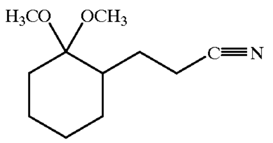

including the stereoisomer:

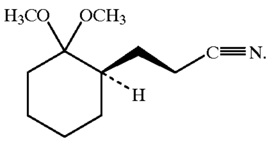

EXAMPLE IV

The compounds defined according to the structure:

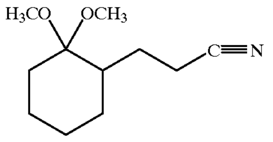

as well as the structure:

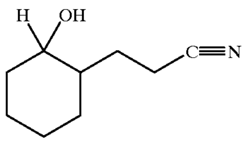

of our invention have very long lasting and intense woody, orris, sweet, coumarinic aromas with spicy, soft floral (muguet) undertones which may be utilized to a great extent in inexpensive, functional products. The following pine fragrance demonstrates the use of these materials in perfume compositions:

| | Parts by Weight | |
|---|---|---|
| Ingredients | IV(A) | IV(B) |
| Isobornyl acetate | 100 | 100 |
| Camphor | 10 | 10 |
| α-Terpineol | 25 | 25 |
| Fir Balsam Absolute (50% in diethyl phthalate) | 20 | 20 |
| Coumarin | 4 | 4 |
| Linalool | 30 | 30 |
| Anethol | 2 | 2 |
| Fenchyl alcohol | 10 | 10 |
| Lemon terpenes washed | 50 | 50 |
| Racemic borneol | 5 | 5 |
| Galbanum oil | 5 | 5 |
| Turpentine Russian | 150 | 150 |
| *Pinus pumilionus* | 50 | 50 |
| Eucalyptol | 50 | 50 |
| 2,2,6-Trimethyl-1-cyclohexene-1-carboxaldehyde | 5 | 5 |
| Maltol (1% in diethyl phthalate) | 5 | 5 |
| The compound having the structure: 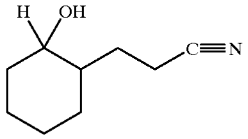 (prepared according to Example II, supra). | 14 | 0 |
| The compound having the structure: 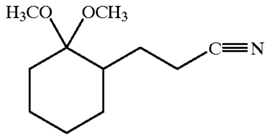 (prepared according to Example III, supra). | 0 | 14 |

The compound having the structure:

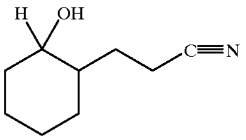

prepared according to Example II adds to this pine fragrance, intense and substantive sweet, coumarinic topnotes with soft, floral (muguet) undertones. Accordingly, the pine formulation of Example IV(A) can be described as "a piney aroma with sweet, coumarinic topnotes and soft, floral (muguet) undertones."

The compound having the structure:

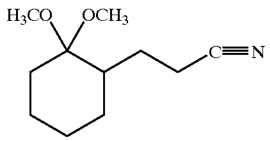

prepared according to Example III, supra, adds to this pine fragrance intense and substantive woody, orris topnotes with spicy undertones. Accordingly, the fragrance of Example IV(B) can be described as "a piney aroma with intense and substantive woody, orris topnotes and spicy undertones."

EXAMPLE V

Cosmetic Powder Preparation

A cosmetic powder is prepared by mixing in a ball mill 100 grams of talcum powder with 0.25 grams of one of the substances set forth in Table II below containing at least one of the α-oxygen-substituted cyclohexane propionitriles of our invention. Each of the cosmetic powders has an excellent aroma as described in Table II below:

TABLE II

| Perfumery Substance | Perfumery Nuance |
|---|---|
| The compound having the structure: 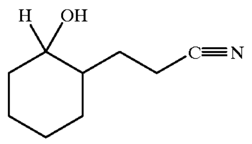 prepared according to Example II. | A sweet, coumarinic aroma with soft, floral (muguet) undertones. |
| The compound having the structure: 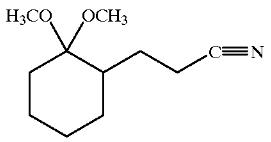 prepared according to Example III. | A woody, orris aroma with spicy undertones. |
| The perfume composition of Example IV(A) | A piney aroma with sweet, coumarinic topnotes and soft, floral (muguet) undertones. |
| The perfume composition of Example IV(B) | A piney aroma with intense and substantive woody, orris topnotes and spicy undertones. |

EXAMPLE VI

Perfumed Liquid Detergent

Concentrated liquid detergents (lysine salt of n-dodecylbenzene sulfonic acid as more specifically described in U.S. Pat. No. 3,948,818 issued on Apr. 6, 1976, the specification for which is incorporated by reference herein) with aromas as set forth in Table II of Example V, supra, are prepared containing 0.10%, 0.15%, 0.20%, 0.25%, 0.30% and 0.35% of each of the substances of Table II of Example V. They are prepared by adding and homogeneously admixing the appropriate quantity of one of the substances of Table II of Example V in the liquid detergent. The detergents all possess excellent aromas as set forth in Table II of Example V.

EXAMPLE VII

Preparation of a Cologne and Handkerchief Perfume

The substances set forth in Table II of Example V are incorporated separately into colognes at concentrations of 2.0%, 2.5%, 3.0%, 3.5%, 4.0%, 4.5% and 5.0% in 75%, 80%, 85% and 90% aqueous food grade ethanol solutions and into handkerchief perfumes at concentrations of 15%, 20%, 25% and 30% in 80%, 85%, 90% and 95% aqueous food grade ethanol solutions. Distinctive aromas as set forth in Table II of Example V, supra, are imparted to the colognes and to the handkerchief perfume compositions at all levels indicated.

EXAMPLE VIII

Preparation of Soap Composition

100 Grams of soap chips (IVORY®, produced by the Procter & Gamble Company of Cincinnati, Ohio) are admixed with 1 gram of each of the substances of Table II of Example V, supra, until homogeneous compositions are obtained. The homogeneous compositions are each separated then heated under 3 atmospheres pressure at 180° C. for a period of 3 hours and the resulting liquid samples are placed in soap molds. The resulting soap cakes, on cooling, manifest excellent long lasting aromas as set forth in Table II of Example V.

EXAMPLE IX

Preparation of Solid Detergent Compositions

Detergents are prepared from the following ingredients according to Example II of Canadian Letters Patent No. 1,007,948, the specification for which is incorporated by reference herein:

| Ingredients | Parts by Weight |
|---|---|
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table II of Example V. Each of the detergent samples has excellent aromas as set forth in Table II of Example V.

EXAMPLE X

Dryer-added Fabric Softener Article

Utilizing the procedure of Example II at column 15 of U.S. Pat. No. 3,623,396, the specification for which is incorporated by reference herein, a non-woven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation:
   57%—$C_{20}$–$C_{22}$ HAPS;
   22%—isopropyl alcohol;
   20%—antistatic agent; and
   1%—of one of the substances of Table II of Example V, supra.

Fabric softening compositions containing one of the substances of Table II of Example V consist essentially of a substrate having a weight of about 3 grams per 100 square inches of substrate coating having a weight of about 1.85 grams per 100 square inches; and a outer coating having a weight of about 1.4 grams per 100 square inches thereby providing a total aromatized substrate and an outer coating weight ratio of about 1:1 by weight of the substrate.

Pleasant aromas as set forth in Table II of Example V are imparted to the headspace in the dryer on operation thereof using the said dryer-added fabric softening non-woven fabric.

What is claimed is:

1. A composition of matter comprising a perfume base, a cologne base or a perfumed article base and a nitrile compound selected from the group consisting of α-oxygen-substituted cyclohexane propionitriles defined according to the structure:

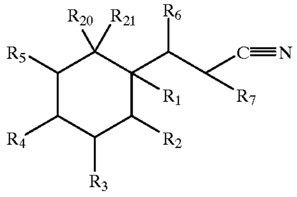

wherein $R_{20}$ and $R_{21}$ are the same or different $C_1$–$C_4$ lower alkoxy; or wherein $R_{20}$ is hydrogen and $R_{21}$ is hydroxy, $C_1$–$C_3$ lower alkoxy or $C_1$–$C_3$ lower acyloxy; and wherein $R_1$, $R_2$, $R_3$, $R_4$, $R_5$, $R_6$ and $R_7$ are the same or different hydrogen or $C_1$–$C_4$ lower alkyl.

2. The composition of claim 1 wherein the nitrile compound has the structure:

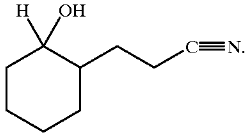

3. A compound having the structure:

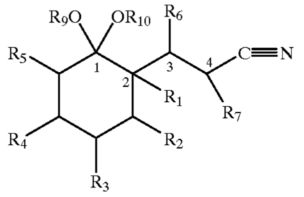

wherein $R_9$ and $R_{10}$ are the same or different $C_1$–$C_4$ lower alkyl and wherein $R_1$, $R_2$, $R_3$, $R_4$, $R_5$, $R_6$ and $R_7$ are the same or different $C_1$–$C_4$ lower alkyl or hydrogen.

4. The compound of claim 3 having the structure:

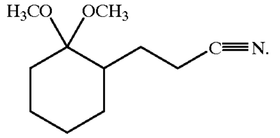

5. A process for preparing a compound defined according to claim 3 comprising the step of intimately admixing in acid media a trialkyl orthoformate having the structure:

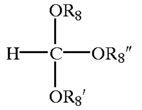

wherein $R_8$, $R_8$' and $R_8$" are the same or different $C_1$–$C_4$ lower alkyl, with a compound having the structure:

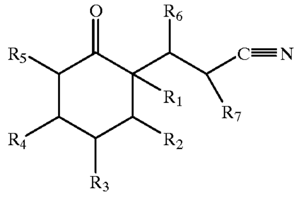

according to the reaction:

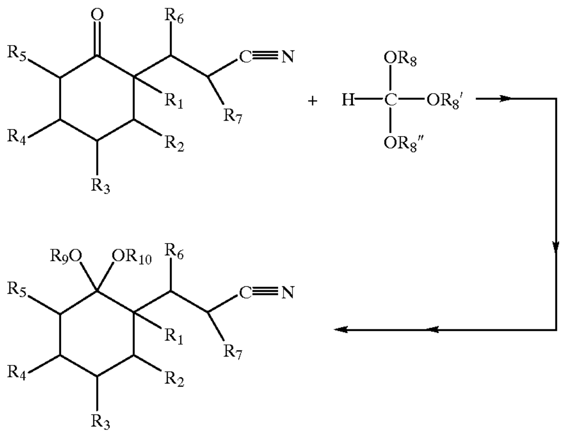

and isolating from the reaction mass the compound having the structure:

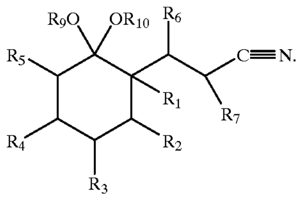

6. A process for preparing the compound of claim 4 comprising the step of intimately admixing in acid media trimethyl orthoformate having the structure:

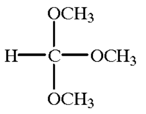

with the compound having the structure:

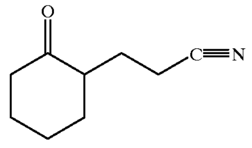

according to the reaction:

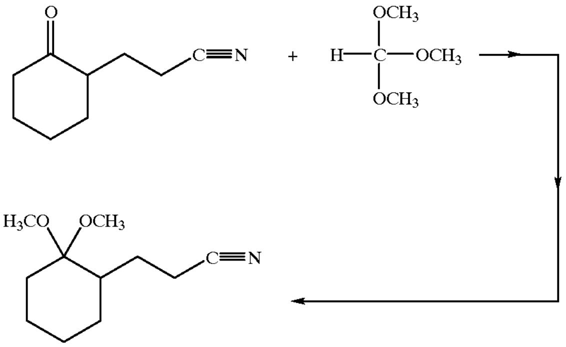

and isolating from the reaction mass the compound having the structure:

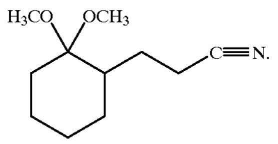

7. A process for augmenting or enhancing the aroma of a perfume composition, perfumed article or cologne comprising the step of intimately admixing with a perfume composition base, a perfumed article base or a cologne base an aroma augmenting or enhancing quantity of at least one nitrile compound defined according to claim 1.

8. A process for augmenting or enhancing the aroma of a perfume composition, perfumed article or cologne comprising the step of intimately admixing with a perfume composition base, a perfumed article base or a cologne base an aroma augmenting or enhancing quantity of the nitrile compound defined according to claim 2.

9. A process for augmenting or enhancing the aroma of a perfume composition, perfumed article or cologne comprising the step of intimately admixing with a perfume composition base, a perfumed article base or a cologne base an aroma augmenting or enhancing quantity of the compound defined according to claim 3.

10. A perfume composition comprising a perfume base and intimately admixed therewith an aroma augmenting or enhancing quantity of at least one α-oxygen-substituted cyclohexane propionitrile defined according to claim 1.

11. A perfumed article comprising a perfumed article base and intimately admixed therewith an aroma augmenting, enhancing or imparting quantity and concentration of the nitrile compound defined according to claim 2.

12. A cologne comprising water, ethanol and at least one nitrile compound defined according to claim 1.

13. A cologne comprising water, ethanol and an aroma augmenting, enhancing or imparting quantity of the nitrile compound defined according to claim 2.

14. A cologne composition comprising water, ethanol and an aroma augmenting, enhancing or imparting quantity of the compound defined according to claim 3.

15. A perfumed article comprising a perfumed article base and at least one α-oxygen-substituted cyclohexane propionitrile defined according to claim 3 in an augmenting, enhancing or imparting quantity and concentration.

16. A perfumed article comprising a perfumed article base and at least one α-oxygen-substituted cyclohexane propionitrile defined according to claim 4 in an augmenting, enhancing or imparting quantity and concentration.

17. A cologne composition comprising water, ethanol and an aroma augmenting, enhancing or imparting quantity of the compound defined according to claim 4.

18. A perfume composition comprising a perfume base and intimately admixed therewith an aroma augmenting or enhancing quantity of at least one α-oxygen-substituted cyclohexane propionitrile defined according to claim 3.

19. A perfume composition comprising a perfume base and intimately admixed therewith an aroma augmenting or enhancing quantity of at least one α-oxygen-substituted cyclohexane propionitrile defined according to claim 4.

* * * * *